US007879356B2

(12) United States Patent  
Cohn et al.

(10) Patent No.: US 7,879,356 B2
(45) Date of Patent: Feb. 1, 2011

(54) POLYMERIC COMPOSITIONS

(75) Inventors: Daniel Cohn, Jerusalem (IL); Theodor Stern, Jerusalem (IL); Avraham Levi, Shoham (IL)

(73) Assignee: Synthemed, Inc., Iselin, NJ (US)

( * ) Notice: Subject to any disclaimer, the term of this patent is extended or adjusted under 35 U.S.C. 154(b) by 0 days.

(21) Appl. No.: 09/804,745

(22) Filed: Mar. 13, 2001

(65) Prior Publication Data

US 2001/0009662 A1 Jul. 26, 2001

Related U.S. Application Data

(60) Division of application No. 09/006,664, filed on Jan. 13, 1998, now Pat. No. 6,211,249, which is a continuation-in-part of application No. 08/890,802, filed on Jul. 11, 1997, now Pat. No. 6,136,333.

(51) Int. Cl.
A61K 9/14 (2006.01)
A61K 47/00 (2006.01)
A61K 47/30 (2006.01)
C08G 63/08 (2006.01)

(52) U.S. Cl. .................. 424/486; 514/772.1; 514/772.3; 525/450

(58) Field of Classification Search ............... 514/772.1, 514/772.3; 525/408, 450; 424/486
See application file for complete search history.

(56) References Cited

U.S. PATENT DOCUMENTS

| | | | |
|---|---|---|---|
| 3,890,253 A | 6/1975 | Takeshita et al. | |
| 3,912,692 A | 10/1975 | Casey et al. | |
| 3,997,512 A | 12/1976 | Casey et al. | |
| 4,048,256 A | 9/1977 | Casey et al. | |
| 4,081,494 A * | 3/1978 | Sakai et al. | 525/444 |
| 4,094,797 A * | 6/1978 | Newkirk et al. | 428/395 |
| 4,095,600 A | 6/1978 | Casey et al. | |
| 4,118,470 A | 10/1978 | Casey et al. | |
| 4,122,129 A | 10/1978 | Casey et al. | |
| 4,343,931 A | 8/1982 | Barrows | |
| 4,346,709 A | 8/1982 | Schmitt | |
| 4,429,080 A | 1/1984 | Casey et al. | |
| 4,438,253 A | 3/1984 | Casey et al. | |
| 4,452,973 A | 6/1984 | Casey et al. | |
| 4,529,792 A | 7/1985 | Barrows | |
| 4,661,530 A | 4/1987 | Gogolewski et al. | |
| 4,705,820 A | 11/1987 | Wang et al. | |
| 4,716,203 A | 12/1987 | Casey et al. | |
| 4,781,183 A | 11/1988 | Casey et al. | |
| 4,788,979 A | 12/1988 | Jarrett et al. | |
| 4,791,929 A | 12/1988 | Jarrett et al. | |
| 4,826,945 A | 5/1989 | Cohn et al. | |
| 4,842,851 A | 6/1989 | Grollier et al. | |
| 4,857,602 A | 8/1989 | Casey et al. | |
| 4,877,539 A | 10/1989 | Ploog et al. | |
| 4,882,168 A | 11/1989 | Casey et al. | |
| 4,902,834 A | 2/1990 | Otten et al. | |
| 4,911,926 A | 3/1990 | Henry et al. | |
| 4,937,254 A | 6/1990 | Sheffield et al. | |
| 4,988,777 A | 1/1991 | Hergenrother et al. | |
| 5,075,115 A | 12/1991 | Brine | |
| 5,080,665 A | 1/1992 | Jarrett et al. | |
| 5,093,351 A | 3/1992 | Batt | |
| 5,100,992 A | 3/1992 | Cohn et al. | |
| 5,133,755 A | 7/1992 | Brekke | |
| 5,202,413 A | 4/1993 | Spinu | |
| 5,278,255 A | 1/1994 | Weaver, Jr. et al. | |
| 5,288,496 A | 2/1994 | Lewis | |
| 5,314,969 A | 5/1994 | Imaizumi et al. | |
| 5,380,536 A | 1/1995 | Hubbell et al. | |
| 5,380,813 A | 1/1995 | Seppala et al. | |
| 5,410,016 A | 4/1995 | Hubbell et al. | |
| 5,429,826 A * | 7/1995 | Nair et al. | 424/501 |
| 5,447,966 A | 9/1995 | Hermes et al. | |
| 5,525,671 A * | 6/1996 | Ebato et al. | 525/53 |
| 5,529,914 A | 6/1996 | Hubbell et al. | |
| 5,578,325 A * | 11/1996 | Domb et al. | 424/501 |

(Continued)

FOREIGN PATENT DOCUMENTS

EP 0737703 A2 10/1996

(Continued)

OTHER PUBLICATIONS

Wiseman, "Polymers for the Prevention of Surgical Adhesions"; *Polymeric Site-specific Pharmacotherapy*, pp. 369-421, A.J. Domb, ed.., John Wiley & Sons, 1994.

(Continued)

*Primary Examiner*—Johann R Richter
*Assistant Examiner*—Abigail Fisher
(74) *Attorney, Agent, or Firm*—Henry D. Coleman; R. Neil Sudol; William J. Sapone

(57) ABSTRACT

The present invention relates to novel bioabsorbable polymeric compositions based upon AB polyester polyether or related diblocks and triblocks. Compositions according to the present invention may be used in medical applications, for example, for reducing or preventing adhesion formation subsequent to medical procedures such as surgery, for producing surgical articles including stents and grafts, as coatings, sealants, lubricants, as transient barriers in the body, for materials which control the release of bioactive agents in the body, for wound and burn dressings and producing biodegradable articles, among numerous others.

19 Claims, No Drawings

U.S. PATENT DOCUMENTS

| | | | |
|---|---|---|---|
| 5,626,863 A | | 5/1997 | Hubbell et al. |
| 5,683,723 A | * | 11/1997 | Spenlehauer et al. ........ 424/501 |
| 5,711,958 A | | 1/1998 | Cohn et al. |
| 5,834,274 A | | 11/1998 | Hubbell et al. |
| 5,843,743 A | | 12/1998 | Hubbell et al. |
| 5,854,382 A | | 12/1998 | Loomis |
| 5,858,746 A | | 1/1999 | Hubbell et al. |
| 5,986,043 A | | 11/1999 | Hubbell et al. |
| 6,005,020 A | | 12/1999 | Loomis |
| 6,028,164 A | | 2/2000 | Loomis |
| 6,060,582 A | | 5/2000 | Hubbell et al. |
| 6,201,065 B1 | | 3/2001 | Pathak et al. |
| 6,211,249 B1 | | 4/2001 | Cohn et al. |
| 6,306,922 B1 | | 10/2001 | Hubbell et al. |
| 6,316,522 B1 | | 11/2001 | Loomis et al. |
| 6,387,977 B1 | | 5/2002 | Sawhney et al. |
| 6,403,758 B1 | | 6/2002 | Loomis |
| 6,410,645 B1 | | 6/2002 | Pathak et al. |
| 6,465,001 B1 | | 10/2002 | Hubbell et al. |
| 6,514,534 B1 | | 2/2003 | Sawhney |
| 6,534,560 B2 | | 3/2003 | Loomis et al. |
| 6,566,406 B1 | | 5/2003 | Pathak et al. |
| 6,602,975 B2 | | 8/2003 | Hubbell et al. |
| 6,632,446 B1 | | 10/2003 | Hubbell et al. |
| 6,639,014 B2 | | 10/2003 | Pathak et al. |
| 6,660,827 B2 | | 12/2003 | Loomis et al. |
| 6,703,037 B1 | | 3/2004 | Hubbell et al. |
| 6,743,446 B2 | | 6/2004 | Schwendeman et al. |
| 6,818,018 B1 | | 11/2004 | Sawhney |

FOREIGN PATENT DOCUMENTS

| | | |
|---|---|---|
| JP | 08-295727 | 11/1996 |
| WO | WO95/03357 | 2/1995 |

OTHER PUBLICATIONS

DiZerega and Rodgers, "The Peritoneum", ch. 9-10, pp. 369-420, Springer-Verlag, 1994.

Sawhney et al., "Bioerodible Hydrogels Based on Photopolymerized Poly(ethylene glycol)-co-poly (alpha-hydroxy acid) Diacrylate Macromers"; *Macromolecules*, 26(4):581-587, 1993.

West and Hubbell, Comparison of covalently and physically cross-linked polyethylene glycol-based hydrogels for the prevention of postoperative adhesions in a rat model:; *Biomaterials*, 16(15);1153-1156, 1995.

Sawhney et al., "Prevention of Postoperative Peritoneal Adhesions Using In Situ Photopolymerization of Novel Biodegradable Hydrogels"; pre-publication submitted to *Fertility and Sterility*, 1992.

* cited by examiner

POLYMERIC COMPOSITIONS

RELATED APPLICATIONS

This application is a division of U.S. application Ser. No. 09/006,664, filed Jan. 13, 1998 now U.S. Pat. No. 6,211,249, which is a continuation-in-part application of Ser. No. 08/890,802, filed Jul. 11, 1997, now U.S. Pat. No. 6,136,333.

The present invention relates to novel bioabsorbable polymeric compositions based upon AB polyester polyether or related diblocks. Compositions according to the present invention may be used in medical applications, for example, for reducing or preventing adhesion formation subsequent to medical procedures such as surgery, for producing surgical articles including stents and grafts, as coatings, sealants, lubricants, as transient barriers in the body, for materials which control the release of bioactive agents in the body, for wound and burn dressings and producing biodegradable articles, among numerous others.

BACKGROUND OF THE INVENTION

The desire to find improved polymeric compositions which can be used for specific medical and environmental applications is ever present. There is a continuous search for new, improved biodegradable polymers to provide enhanced materials which are biocompatible, have good bioabsorbtive/biodegradable properties, appropriate mechanical and physical properties and related structural characteristics which find use in the prescribed application. Materials which provide superior characteristics as well as flexibility in formulation and manufacture are especially desirable.

Early biodegradable/bioabsorbable polymers focused on polylactic and/or polyglycolic acid homopolymers or copolymers which were used primarily in bioabsorbable sutures. These early polymers suffered from the disadvantage that the polymers tended to be hard or stiff and often brittle with little flexibility. In addition, the kinetics of their degradation tended to be slow in certain applications, necessitating research on polymers with faster degradation profiles.

A number of other copolymers utilizing lactic acid, glycolic acid, $\epsilon$-caprolactone, poly(orthoesters) and poly(orthocarbonates), poly(esteramides) and related polymers have been synthesized and utilized in medical applications with some measure of success. The polymers tend to be limited, however, by disadvantages which appear in one or more of the following characteristics: flexibility, strength, extensibility, hardness/softness, biocompatibility, biodegradability, sterilizability, ease of formulation over a wide range of applications and tissue reactivity.

Recent investigative attention has centered on the production of ACA triblock polymeric compositions which are derived from blocks of poly(oxy)alkylene and polyhydroxycarboxylic acids. These formulations, among others have exhibited favorable characteristics for use to reduce and/or prevent adhesion formulation secondary to surgery and other medical applications.

OBJECTS OF THE INVENTION

It is an object of the present invention to provide novel polymeric materials which may be used in a variety of medical, environmental and other applications where biodegradability/bioerodability is an important feature of the application.

It is an additional object of the invention to provide polymeric materials which may be manufactured in film form and other solid structures such as rods, cylinders, porous structures such as foams, dispersions, viscous solutions, liquid polymers, pastes, sprays or gels which may be administered easily or adapted for use in a wide range of applications.

It is yet another object of the invention to provide polymeric materials which may be used to substantially prevent adhesions and which may be effective for delivering bioactive agents.

It is yet an additional object of the invention to provide bioabsorbable polymeric materials which can be produced in a variety of formulations which have acceptable strength, may be reactive or non-reactive with patient tissue depending upon the desired application and are bioabsorbable.

It is yet another object of the present invention to provide polymeric barriers which can be used in various forms, e.g., films, other structures such as rods and cylinders, foams, gels, dispersions, liquid polymers, pastes, sprays or viscous solutions, to provide flexibility in administration and use in a variety of applications, including medical applications, environmental applications and other applications.

These and/or other objects of the invention may be readily gleaned from the detailed description of the present invention which follows.

SUMMARY OF THE INVENTION

The present invention relates to multiblock polymeric materials which utilize AB diblocks as building blocks for the polymeric materials.

The present invention preferably relates to polymeric compositions comprising coupled or crosslinked poly(ester)/polyether AB or related AB diblocks, where A is a polyester unit derived from the polymerization of monomers and B is a monofunctional hydroxyl, amine or carboxyl containing molecule (which may be monomeric or polymeric) which is end-capped with a non-reactive group, such that the hydroxyl, amine or carboxyl-containing molecule initiates the polymerization of the monomers to form the polyester unit (A block). In preferred embodiments according to the present invention, the polyester unit A is derived from the polymerization of monomers selected from the group consisting of lactic acid, lactide, glycolic acid, glycolide, $\beta$-propiolactone, $\epsilon$-caprolactone, $\delta$-glutarolactone, $\delta$-valerolactone, $\beta$-butyrolactone, pivalolactone, $\alpha,\alpha$-diethylpropiolactone, ethylene carbonate, trimethylene carbonate, $\gamma$-butyrolactone, p-dioxanone, 1,4-dioxepan-2-one, 3-methyl-1,4-dioxane-2,5-dione, 3,3,-dimethyl-1-4-dioxane-2,5-dione, cyclic esters, of $\alpha$-hydroxybutyric acid, $\alpha$-hydroxyvaleric acid, $\alpha$-hydroxyisovaleric acid, $\alpha$-hydroxycaproic acid, $\alpha$-hydroxy-$\alpha$-ethylbutyric acid, $\alpha$-hydroxyisocaproic acid, $\alpha$-hydroxy-$\alpha$-methyl valeric acid, $\alpha$-hydroxyheptanoic acid, $\alpha$-hydroxystearic acid, $\alpha$-hydroxylignoceric acid, salicylic acid and mixtures, thereof. B may be derived from any monofunctional hydroxyl, amine or carboxyl containing molecule which is capable of initiating polymerization of the monomers which comprise the A block. In preferred aspects of the present invention, the monofunctional molecule (which is also referred to as a "monofunctional initiator molecule") is a $C_1$ to $C_{12}$ amine, alcohol or carboxylic acid. The alcohol, amine or carboxylic acid may be an alkyl amine, alcohol or carboxylic acid, an aryl amine, alcohol or carboxylic acid, an aralkyl amine, alcohol or carboxylic acid or a substituted alkyl amine, alcohol or carboxylic acid, substituted aryl amine, alcohol or carboxylic acid or a substituted aralkyl amine, alcohol or carboxylic acid. In alternative embodiments, the monofunctional initiator molecule is a poly(oxyalkylene) molecule or a poly(oxyalkylene)-containing molecule, preferably poly (ethylene glycol), varying in molecular weight from as low as 100 (diethylene glycol) to hundreds of thousands or more, with a preferred molecular weight ranging from about 550 to about 5,000 or more.

The AB diblocks described above may be utilized without further modification, or preferably, they may be coupled with a chain-extender or coupling agent as described in more detail herein to produce coupled diblocks or multiblocks according to the present invention. Polymeric compositions according to the present invention are advantageously end-capped with inert groups, i.e. they preferably do not contain any reactive groups at their ends which will participate in any reaction. By relying on end-capping with inert groups, the present compositions unexpectedly attain a storage stability, whether in solid form or solution, which is significantly enhanced compared to compositions which are end-capped with reactive groups such as hydroxyl, amine or carboxylic acid groups.

The present invention relates to a polymer of the chemical structure:

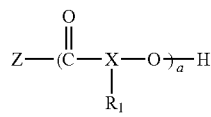

where a is a positive integer,

X is a $C_1$-$C_8$ alkylene group, preferably a $C_1$ (CH) alkylene group, $R_1$ is H or $CH_3$, preferably H when X is a $C_2$-$C_8$ alkylene group and Z is derived from an amine- or hydroxyl-containing monofunctional monomeric or polymeric compound end-capped with an amine or hydroxyl group, the amine- or alcohol-containing compound preferably being selected from an alkyl (preferably, $C_1$ to $C_{12}$) amine or alcohol, an aryl amine or alcohol, an aralkyl amine or alcohol or a substituted alkyl (preferably, $C_1$ to $C_{12}$) amine or alcohol, a substituted aryl amine or alcohol, a substituted aralkyl amine or alcohol, a blocking group or a C=C containing group.

Z is preferably represented by the structure M—(O—R—)$_m$—Y, where m is a positive integer, Y is O or NH, R is a $C_2$ to $C_{10}$ alkylene group and is preferably an ethylene group and/or propylene group, and M is a non-reactive group or a group containing a blocking group or a —C=C— group, preferably a group selected from a $C_1$ to $C_{12}$ alkyl group, an aryl group, an aralkyl group or a substituted $C_1$ to $C_{12}$ alkyl group, aryl group, aralkyl group, a blocking group or a C=C containing group.

The present invention also relates to a polymeric composition of the chemical structure:

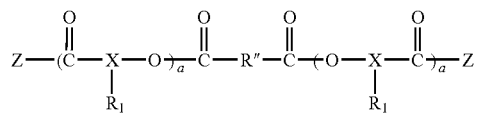

where a is a positive integer,

Z is derived from an amine- or hydroxyl-containing monofunctional monomeric or polymeric compound end-capped with an amine or hydroxyl group, the amine- or alcohol-containing compound preferably being selected from an alkyl (preferably, $C_1$ to $C_{12}$) amine or alcohol, an aryl amine or alcohol, an aralkyl amine or alcohol or a substituted alkyl (preferably, $C_1$ to $C_{12}$) amine or alcohol, a substituted aryl amine or alcohol, or a substituted aralkyl amine or alcohol, a blocking group or a C=C containing group, X is a $C_1$-$C_8$ alkylene group, preferably a $C_1$ (CH) alkylene group, R" is a $C_0$ to $C_{12}$ alkylene group or a hydroxyl or carboxylic acid substituted alkyl group, a cycloalkyl, a hydroxyl-containing cycloalkyl, or cycloalkyl-containing group, an aryl or aryl-containing group, an oligoester or polyester, or a polyoxyalkylene chain-containing group, preferably comprised of poly(ethylene oxide), poly(ethylene oxide)-co-poly(propylene oxide) or a poly(ethylene oxide) rich chain, and $R_1$ is H or $CH_3$, preferably H when X is a $C_2$-$C_8$ alkylene group.

Z is preferably represented by the structure M—(O—R—)$_m$—Y, where m is a positive integer, Y is O or NH, R is a $C_2$ to $C_{10}$ alkylene group, preferably an ethylene group ($C_2$) and/or propylene group ($C_3$), M is a non-reactive group or a group containing a blocking group or a —C=C— group, preferably, a $C_1$ to $C_{12}$ alkyl group, an aryl group, an aralkyl group or a substituted $C_1$ to $C_{12}$ alkyl group, an aryl group, an aralkyl group, a blocking group or a C=C containing group. More preferably, M is methyl or ethyl.

The present invention also relates to a polymeric composition according to the chemical structure:

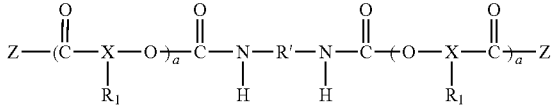

where a is a positive integer,

Z is derived from an amine- or hydroxyl-containing monofunctional monomeric or polymeric compound end-capped with an amine or hydroxyl group, the amine- or alcohol-containing compound preferably being selected from an alkyl (preferably, $C_1$ to $C_{12}$) amine or alcohol, an aryl amine or alcohol, an aralkyl amine or alcohol or a substituted alkyl (preferably, $C_1$ to $C_{12}$) amine or alcohol, a substituted aryl amine or alcohol, or a substituted aralkyl amine or alcohol, a blocking group or a C=C containing group, X is a $C_1$-$C_8$ alkylene group, preferably a $C_1$ (CH) alkylene group, R' is a $C_2$ to $C_{12}$ alkylene group, a cycloalkyl or cycloalkyl-containing group, an aryl or aryl-containing group, 4,4'-diphenylmethane, toluene, naphthalene, 4,4'-dicyclohexylmethane, cyclohexyl, 3,3'-dimethylphenyl, 3,3'-dimethyldiphenylmethane, 4,6'-xylylene, 3,5,5-trimethylcyclohexyl, 2,2,4-trimethylhexamethylene or p-phenylene or a poly(ethylene oxide) containing or poly(ethylene oxide) rich chain and $R_1$ is H or $CH_3$, preferably H when X is a $C_2$-$C_8$ alkylene group.

Z is preferably represented by the structure M—(O—R—)$_m$—Y, where m is a positive integer, Y is O or NH, R is a $C_2$ to $C_{10}$ alkylene group, preferably an ethylene group and/or propylene group and M is a non-reactive group or a group containing a blocking group or a —C═C— group, preferably, a $C_1$ to $C_{12}$ alkyl group, an aryl group, an aralkyl group or a substituted $C_1$ to $C_{12}$ alkyl group, an aryl group, an aralkyl group, a blocking group or a C═C containing group. More preferably, M is methyl or ethyl.

The present invention also relates to a polymeric composition according to the chemical structure:

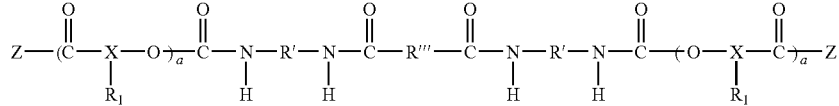

where a is a positive integer,

Z is derived from an amine- or hydroxyl-containing monofunctional monomeric or polymeric compound end-capped with an amine or hydroxyl group, the amine- or alcohol-containing compound preferably being selected from an alkyl (preferably, $C_1$ to $C_{12}$) amine or alcohol, an aryl amine or alcohol, an aralkyl amine or alcohol or a substituted alkyl (preferably, $C_1$ to $C_{12}$) amine or alcohol, a substituted aryl amine or alcohol, or a substituted aralkyl amine or alcohol, a blocking group or a C═C containing group, X is a $C_1$-$C_8$ alkylene group, preferably a $C_1$ (CH) alkylene group, R' is a $C_2$ to $C_{12}$ alkylene group, a cycloalkyl or cycloalkyl-containing group, an aryl or aryl-containing group, 4,4'-diphenylmethane, toluene, naphthalene, 4,4'-dicyclohexylmethane, cyclohexyl, 3,3'-dimethylphenyl, 3,3'-dimethyldiphenylmethane, 4,6'-xylylene, 3,5,5-trimethylcyclohexyl, 2,2,4-trimethylhexamethylene, p-phenylene or a poly(ethylene oxide) containing or poly(ethylene oxide) rich chain, R''' is selected from or derived from the group consisting of a diol, which generates urethane groups upon reaction with a diisocyanate, a diamine, which generates urea groups upon reaction with a diisocyanate or a dicarboxylic acid which generates amide groups upon reaction with a diisocyanate, said diol preferably being selected from the group consisting of $C_2$ to $C_{24}$ (preferably, $C_2$ to $C_{12}$) diols such as ethylene glycol and butanediol, a poly(oxyalkylene) diol compound of the structure —(O—R)$_m$—O— where R is a $C_2$ to $C_{10}$ alkylene group (preferably an ethylene group and/or propylene group) and m is a positive integer, poly(oxyalkylene)-rich diols especially including poly(ethylene oxide)-rich diols, a OH-terminated polycaprolactone or other OH-terminated polyesters, oligoesters or an ACA triblock, wherein in said ACA triblock, A is a polyester unit and C is selected from the group consisting of poly(ethylene oxide), poly(ethylene oxide)-co-poly(propylene oxide), a poly(ethylene oxide) rich chain, a diol and a diamine as set forth above, said diamine being preferably selected from the group consisting of $C_2$ to $C_{24}$ (preferably, $C_2$ to $C_{12}$) diamines, more preferably ethylene diamine and hexamethylene diamine, amino acids, and oligopeptides, said dicarboxylic acid preferably being selected from the group consisting of $C_0$ to $C_{24}$ (preferably, $C_2$ to $C_{12}$) dicarboxylic acids, succinic acid, sebacic acid, adipic acid, malic acid, tartaric acid, oxalic acid, maleic acid, fumaric acid, COOH-terminated polycaprolactone, and COOH-terminated polyesters or oligoesters, and $R_1$ is H or $CH_3$, preferably H when X is a $C_2$-$C_8$ alkylene group.

Z is preferably represented by the structure M—(O—R—)$_m$—Y, where m is a positive integer, Y is O or NH, R is a $C_2$ to $C_{10}$ alkylene group, preferably an ethylene group and/or propylene group and M is a non-reactive group or a group containing a blocking group or a —C═C— group, preferably, a $C_1$ to $C_{12}$ alkyl group, an aryl group, an aralkyl group or a substituted $C_1$ to $C_{12}$ alkyl group, an aryl group, an aralkyl group or a blocking group or a C═C containing group. More preferably, M is methyl or ethyl.

The present invention also relates to a composition comprising a polymer of the chemical structure:

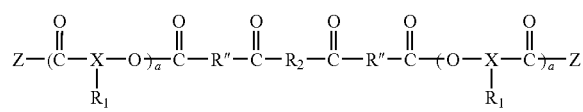

where a is a positive integer,

Z is derived from an amine- or hydroxyl-containing monofunctional monomeric or polymeric compound end-capped with an amine or hydroxyl group, the amine- or alcohol-containing compound preferably being selected from an alkyl (preferably, $C_1$ to $C_{12}$) amine or alcohol, an aryl amine or alcohol, an aralkyl amine or alcohol or a substituted alkyl (preferably, $C_1$ to $C_{12}$) amine or alcohol, a substituted aryl amine or alcohol, or a substituted aralkyl amine or alcohol, a blocking group or a C═C containing group, X is a $C_1$-$C_8$ alkylene group, preferably a $C_1$ (CH) alkylene group, $R_1$ is a hydrogen or methyl group, preferably H when X is a $C_2$-$C_8$ alkylene group, R'' is a $C_0$ to $C_{12}$ alkylene group or a hydroxyl or carboxylic acid substituted alkyl group, a cycloalkyl, a hydroxyl-containing cycloalkyl, or cycloalkyl-containing group, an aryl or aryl-containing group, a carboxyl-terminated oligoester or polyester, or a polyoxyalkylene chain-containing group preferably comprised of poly(ethylene oxide), polyethylene oxide)-co-poly(propylene oxide) or a poly(ethylene oxide) rich chain, and $R_2$ is selected from or derived from the group consisting of a diol, which generates urethane groups upon reaction with a diisocyanate, a diamine, which generates urea groups upon reaction with a diisocyanate or a dicarboxylic acid which generates amide groups upon reaction with a diisocyanate, said diol preferably being selected from the group consisting of $C_2$ to $C_{24}$ (preferably, $C_2$ to $C_{12}$) diols such as ethylene glycol and butanediol, a poly(oxyalkylene) diol compound of the structure —(O—R)$_m$—O— where R is a $C_2$ to $C_{10}$ alkylene group (preferably an ethylene group and/or propylene group) and m is a positive integer, poly(oxyalkylene)-rich diols especially including poly(ethylene oxide)-rich diols, a OH-terminated polycaprolactone or other OH-terminated polyesters, oligoesters or an ACA triblock, wherein in said ACA triblock, A is a polyester unit and C is selected from the group consisting of poly(ethylene oxide), poly(ethylene oxide)-co-poly(propylene oxide), a poly(ethylene oxide) rich chain, a diol and a diamine as set forth above, said diamine being preferably selected from the group consisting of $C_2$ to $C_{24}$ (preferably, $C_2$ to $C_{12}$) diamines, more preferably ethylene diamine and hexamethylene diamine, amino acids, and oligopeptides, said dicarboxylic acid preferably being selected from the group consisting of $C_0$ to $C_{24}$ (preferably, $C_2$ to $C_{12}$) dicarboxylic acids, succinic acid, sebacic acid, adipic acid, malic acid, tartaric acid, oxalic acid, maleic acid, fumaric acid, COOH-terminated polycaprolactone, and COOH-terminated polyesters or oligoesters.

Z is preferably represented by the structure M—(O—R—)$_m$—Y, where m is a positive integer, Y is O or NH, R is a $C_2$ to $C_{10}$ alkylene group, preferably an ethylene group and/or propylene group and M is a non-reactive group or a group containing a blocking group or a —C≡C— group, preferably, a $C_1$ to $C_{12}$ alkyl group, an aryl group, an aralkyl group or a substituted $C_1$ to $C_{12}$ alkyl group, an aryl group, an aralkyl group or a blocking group or a C≡C containing group. More preferably, M is methyl or ethyl.

Other embodiments of the present invention are directed to a composition comprising a polymer of the chemical structure:

R' is a $C_2$ to $C_{12}$ alkylene group, a cycloalkyl or cycloalkyl-containing group, an aryl or aryl-containing group, 4,4'-diphenylmethane, toluene, naphthalene, 4,4'-dicyclohexyl-methane, cyclohexyl, 3,3'-dimethylphenyl, 3,3'-dimethyl-diphenylmethane, 4,6'-xylylene, 3,5,5-trimethylcyclohexyl, 2,2,4-trimethylhexamethylene, p-phenylene, or a poly(oxyalkylene) chain, including a poly(ethylene oxide) containing or poly(ethylene oxide) rich chain, R''' is selected from or derived from the group consisting of a diol, which generates urethane groups upon reaction with a diisocyanate, a diamine, which generates urea groups upon reaction with a diisocyanate or a dicarboxylic acid which generates amide groups upon reaction with a diisocyanate, said diol preferably being selected from the group consisting of $C_2$ to $C_{24}$ (preferably, $C_2$ to $C_{12}$) diols such as ethylene glycol and butanediol, a poly(oxyalkylene) diol compound of the structure —(O—R)$_m$—O— where R is a $C_2$ to $C_{10}$ alkylene group (preferably an ethylene group and/or propylene group) and m is a positive integer, poly(oxyalkylene)-rich diols especially including poly(ethylene oxide)-rich diols, a OH-terminated polycaprolactone or other OH-terminated polyesters, oligoesters or an ACA triblock, wherein in said ACA triblock, A is a polyester unit and C is selected from the group consisting of poly(ethylene oxide), poly(ethylene oxide)-co-poly(propylene oxide), a poly(ethylene oxide) rich chain, a diol and a diamine as set forth above, said diamine being preferably selected from the group consisting of $C_{12}$ to $C_{24}$ (preferably, $C_2$ to $C_{12}$) diamines, more preferably ethylene diamine and hexamethylene diamine, amino acids, and oligopeptides, said dicarboxylic acid preferably being selected from the group consisting of $C_0$ to $C_{24}$ (preferably, $C_2$ to $C_{12}$) dicarboxylic acids, succinic acid, sebacic acid, adipic acid, malic acid, tartaric acid, oxalic acid, maleic acid, fumaric acid, COOH-terminated polycaprolactone, and COOH-terminated polyesters or oligoesters, and $R_1$ is H or $CH_3$, preferably H when X is a $C_2$-$C_8$ alkylene group and preferably $CH_3$ when X is $C_1$.

Z is preferably represented by the structure M—(O—R—)$_m$—Y,

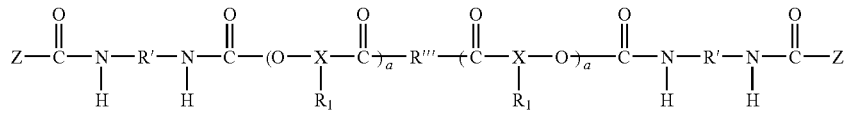

where a is a positive integer,

Z is derived from an amine- or hydroxyl-containing monofunctional monomeric or polymeric compound end-capped with an amine or hydroxyl group, the amine- or alcohol-containing compound preferably being selected from an alkyl (preferably, $C_1$ to $C_{12}$) amine or alcohol, an aryl amine or alcohol, an aralkyl amine or alcohol or a substituted alkyl (preferably, $C_1$ to $C_{12}$) amine or alcohol, a substituted aryl amine or alcohol, or a substituted aralkyl amine or alcohol, a blocking group or a C≡C containing group, X is a $C_1$-$C_8$ alkylene group, preferably a $C_1$ (CH) alkylene-group, where m is a positive integer, Y is O or NH, R is a $C_2$ to $C_{10}$ alkylene group, preferably an ethylene group and/or propylene group and M is a non-reactive group or a group containing a blocking group or a —C≡C— group, preferably, a $C_1$ to $C_{12}$ alkyl group, an aryl group, an aralkyl group or a substituted $C_1$ to $C_{12}$ alkyl group, an aryl group, an aralkyl group or a blocking group or a C≡C containing group. More preferably, M is methyl or ethyl.

Other embodiments of the present invention are directed to a composition comprising a polymer of the chemical structure:

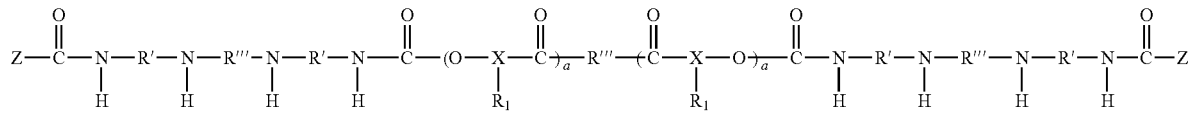

where a is a positive integer,

Z is derived from an amine- or hydroxyl-containing monofunctional monomeric or polymeric compound end-capped with an amine or hydroxyl group, the amine- or alcohol-containing compound preferably being selected from an alkyl (preferably, $C_1$ to $C_{12}$) amine or alcohol, an aryl amine or alcohol, an aralkyl amine or alcohol or a substituted alkyl (preferably, $C_1$ to $C_{12}$) amine or alcohol, a substituted aryl amine or alcohol, or a substituted aralkyl amine or alcohol, a blocking group or a C=C containing group, X is a $C_1$-$C_8$ alkylene group, preferably a $C_1$ (CH) alkylene-group, R' is a $C_2$ to $C_{12}$ alkylene group, a cycloalkyl or cycloalkyl-containing group, an aryl or aryl-containing group, 4,4'-diphenylmethane, toluene, naphthalene, 4,4'-dicyclohexylmethane, cyclohexyl, 3,3'-dimethylphenyl, 3,3'-dimethyldiphenylmethane, 4,6'-xylylene, 3,5,5-trimethylcyclohexyl, 2,2,4-trimethylhexamethylene, p-phenylene, or a poly(oxyalkylene) chain, including a poly(ethylene oxide) containing or poly(ethylene oxide) rich chain, R''' is selected from or derived from the group consisting of a diol, which generates urethane groups upon reaction with a diisocyanate, a diamine, which generates urea groups upon reaction with a diisocyanate or a dicarboxylic acid which generates amide groups upon reaction with a diisocyanate, said diol preferably being selected from the group consisting of $C_2$ to $C_{24}$ (preferably, $C_2$ to $C_{12}$) diols such as ethylene glycol and butanediol, a poly(oxyalkylene) diol compound of the structure —(O—R)$_m$—O— where R is a $C_2$ to $C_{10}$ alkylene group (preferably an ethylene group and/or propylene group) and m is a positive integer, poly(oxyalkylene)-rich diols especially including poly(ethylene oxide)-rich diols, a OH-terminated polycaprolactone or other OH-terminated polyesters, oligoesters or an ACA triblock, wherein in said ACA triblock, A is a polyester unit and C is selected from the group consisting of poly(ethylene oxide), poly(ethylene oxide)-co-poly(propylene oxide), a poly(ethylene oxide) rich chain, a diol and a diamine as set forth above, said diamine being preferably selected from the group consisting of $C_2$ to $C_{24}$ (preferably, $C_2$ to $C_{12}$) diamines, more preferably ethylene diamine and hexamethylene diamine, amino acids, and oligopeptides, said dicarboxylic acid preferably being selected from the group consisting of $C_0$ to $C_{24}$ (preferably, $C_2$ to $C_{12}$) dicarboxylic acids, succinic acid, sebacic acid, adipic acid, malic acid, tartaric acid, oxalic acid, maleic acid, fumaric acid, COOH-terminated polycaprolactone, and COOH-terminated polyesters or oligoesters, and $R_1$ is H or $CH_3$, preferably H when X is a $C_2$-$C_8$ alkylene group and preferably $CH_3$ when X is $C_1$.

Z is preferably represented by the structure M—(O—R—)$_m$—Y, where m is a positive integer, Y is O or NH, R is a $C_2$ to $C_{10}$ alkylene group, preferably an ethylene group and/or propylene group and M is a non-reactive group or a group containing a blocking group or a —C=C— group, preferably, a $C_1$ to $C_{12}$ alkyl group, an aryl group, an aralkyl group or a substituted $C_1$ to $C_{12}$ alkyl group, an aryl group, an aralkyl group or a blocking group or a C=C containing group. More preferably, M is methyl or ethyl.

It is noted that in each of the above polymeric chemical formulas Z may also be derived from a monofunctional carboxylic acid. In such formulations, the chemical structure of the resulting polymer will reflect that initiation. Thus, AB diblocks which result from the initiation of a polyester chain by a monofunctional acid will be end-capped with a carboxylate (carboxylic acid) group and then coupled with a diisocyanate (to produce a resulting amide-containing group), a diol (to produce an ester-containing group) a diamine (to produce an amide-containing group) or, in certain instances, a hydroxylamine (which produces an ester group on one end of the hydroxyl amine and an amide group on the other end of the hydroxylamine. Accordingly, multiblocks which are based upon AB diblocks and coupled with complex couplers, will produce polymers which are analogues to those which are set forth hereinabove. One of ordinary skill in the art, within the teachings of the scope of the present invention, may readily produce numerous polymeric compounds which have chemical structures which are analogous to those which are set forth in detail hereinabove, but which utilize a monofunction carboxylic acid compound to initiate polymerization of the polyester A block.

The present invention also relates to polymeric compositions comprising the reaction product of a diol, diamine or dicarboxylic acid (as otherwise defined in the present invention) with a coupling agent in about a 1:2 mole ratio, with the resulting product being reacted with a monofunctional hydroxyl, amine or carboxylic acid containing compound to produce a pentamer. The diol, diamine or dicarboxylic acid in this aspect of the present invention may be any compound (including monomeric or polymeric compounds) which contain two functional groups and is reactive with one or more chain-extenders or coupling agents. In this aspect of the present invention, the chain-extender or coupling agent is used in a molar excess, preferably in a molar ratio of about 1 mole of diol, diamine or dicarboxylic acid to about 2 moles chain extender or coupling agent. The resulting intermediate product, which contains two reactive groups from the chain extender or coupling agent is thereafter reacted with a monofunctional alcohol, amine or carboxylic compound (which may be monomeric or polymeric) to produce a pentameric product according to the present invention. It is noted that in this aspect of the present invention, the diol, diamine or dicarboxylic acid compound which is used may be a ACA triblock, where A is a polyester unit and C is a compound selected from the group consisting of a diol, a diamine and a dicarboxylic acid compound. In this aspect of the invention, the diol is preferably selected from the group consisting of $C_2$ to $C_{24}$ (preferably, $C_2$ to $C_{12}$) diols including ethylene glycol and butanediol, a poly(oxyalkylene) diol compound of the structure —$(O-R)_m$—O— where R is a $C_2$ to $C_{10}$ alkylene group (preferably an ethylene group and/or propylene group) and m is a positive integer, poly(oxyalkylene)-rich diols especially including poly(ethyl ene oxide)-rich diols, OH-terminated polycaprolactone, OH-terminated polyesters or oligoesters, the diamine is preferably selected from the group consisting of $C_2$ to $C_{24}$ (preferably, $C_2$ to $C_{12}$) diamines including ethylene diamine and hexamethylene diamine, amino acids, and oligopeptides and the dicarboxylic acid is preferably selected from the group consisting of $C_2$ to $C_{24}$ (preferably, $C_2$ to $C_{12}$) dicarboxylic acids, including succinic acid, pimelic acid, azelaic acid, sebacic acid, adipic acid, malic acid, tartaric acid oxalic acid, maleic acid, fumaric acid, COOH-terminated polycaprolactone, and COOH-terminated polyesters or oligoesters. In preferred aspects of this invention, the ACA triblock is comprised of A blocks which are comprised of oligoesters or polyesters and C blocks which are comprised of poly(oxy)alkylene.

In a particular method aspect according to the present invention, in one aspect, the present invention comprises administering or affixing to an area in a patient's body at risk of developing adhesions, a polymeric composition comprising AB diblocks (preferably, as di-diblocks, as discussed in greater detail herein) or ACA triblocks which are chain-extended, coupled and/or crosslinked and contain sufficient polyethylene oxide character to promote anti-adhesion characteristics. In this aspect of the present invention, preferably, the A blocks comprise aliphatic ester units, more preferably derived from hydroxy acid units or their cyclic dimers and the like, even more preferably α-hydroxy acid units. In many embodiments, the method comprises administering the instant polymer compositions to a site within the patient's body which has been subjected to surgical repair or excision. In the present invention, the polymeric material provides a barrier to prevent adhesions from forming. After this period of protection, the polymer will degrade and will be resorbed within the patient's body and/or excreted from the patient's body. According to the present method, problems associated with non-absorption or foreign body reactions are significantly reduced or prevented.

The polymers according to the present invention may be used in various forms such as films, other structures including rods, cylinders, foams, pastes, dispersions, viscous solutions, liquid polymers, sprays or gels. Polymers according to the present invention may be used in a broad array of applications, including, for example, in medical applications, for example, for reducing or preventing adhesion formation subsequent to medical procedures such as surgery, for producing surgical articles including stents and grafts, as coatings, sealants, lubricants, as transient barriers in the body, for materials which control the release of bioactive agents in the body, wound and burn dressings and producing biodegradable articles, among numerous others.

The form a polymer takes will obviously depend upon the application for which such polymer is used. In the case of preventing or reducing the occurrence of adhesion at a surgical site, the form a polymer takes at the surgical site will depend upon the type of surgery which has been performed or the condition which is to be treated and the site to be treated. In addition, the need to deliver the polymer to a particular site within the body may be determinative of the form in which the polymer is delivered. In certain aspects according to the present invention, the present method may be used after surgery to prevent tissue adhesion which occurs during the initial phases of post-surgical repair. Thus, in all applications where tissue is being repaired or excised, certain polymers according to the present invention find utility to prevent adhesions. In certain applications according to the present invention, the polymers are may be used to prevent tissue to tissue adhesion and adhesions between tissues and implants or devices, which occur after surgical procedures, as well as other conditions, including certain disease states.

In the anti-adhesion aspects according to the present invention, the present polymers preferably are based on polyester/poly(oxyalkylene) ACA triblocks or AB diblocks (including AB multiblocks, thereof), where A is a polymer preferably comprising aliphatic ester units, which are preferably derived from hydroxy acid units or their cyclic dimers and the like, even more preferably α-hydroxy acid units or their cyclic dimers and the like, such as a related ester or lactone. Preferably, the A block comprises α-hydroxyacid units derived from an aliphatic α-hydroxy carboxylic acid or a related acid, ester or similar compound such as, for example, lactic acid, lactide, glycolic acid, glycolide, or a related aliphatic hydroxycarboxylic acid or ester (lactone) such as, for example, β-propiolactone, ε-caprolactone, δ-glutarolactone, δ-valerolactone, β-butyrolactone, pivalolactone, α,α-diethylpropiolactone, ethylene carbonate, trimethylene carbonate, γ-butyrolactone, p-dioxanone, 1,4-dioxepan-2-one, 3-methyl-1,4-dioxane-2,5-dione, 3,3,-dimethyl-1-4-dioxane-2,5-dione, cyclic esters of α-hydroxybutyric acid, α-hydroxyvaleric acid, α-hydroxyisovaleric acid, α-hydroxycaproic acid, α-hydroxy-α-ethylbutyric acid, α-hydroxyisocaproic acid, α-hydroxy-α-methyl valeric acid, α-hydroxyheptanoic acid, α-hydroxystearic acid, α-hydroxylignoceric acid, salicylic acid and mixtures, thereof. The use of α-hydroxyacids in the present invention is preferred. The A block of the triblocks and diblocks (and multiblocks, thereof) used in the present invention preferably comprises a poly(α-hydroxy-carboxylic acid), for example, poly(glycolic acid), poly(L-lactic acid) and poly(D,L-lactic acid), because these polymers will degrade and produce monomeric units which may be metabolized by the patient. In this anti-adhesion method aspect of the present invention, the B block in the triblocks used in the present invention is preferably a hydroxyl, carboxylic acid or amine terminated poly(oxyalkylene) block (preferably, hydroxyl terminated) and is more preferably either a poly(ethylene oxide) homopolymer or poly(ethylene oxide)-co-poly(propylene oxide) block copolymer.

The triblocks or diblocks (including multiblocks, thereof) described above are preferably end-capped with hydroxyl or amine groups and are chain-extended or coupled using difunctional chain extenders such as diisocyanates, dicarboxylates, diesters or diacyl halide groups in order to couple the triblocks or diblocks into high molecular weight chains. In the case of diblocks, these are coupled with difunctional chain extenders in much the same way that triblocks are chain extended with the same chain extenders. Alternatively, the triblocks may be end-capped with groups such as carboxylic acid moieties or ester groups (which may be reacted directly as ester groups, activated as "active" ester groups or converted to active acyl groups such as acyl halides) or isocyanate groups and then reacted with difunctional chain extenders such as diols, diamines, hydroxylamines, or polyoxyethylene (polyethylene glycol) or poly(ethylene oxide)-co-poly(propylene oxide) block copolymer chain extenders (especially, in the case of water soluble or water dispersible gels, dispersions or viscous solutions) among others, to produce chain extended polymers preferably having high molecular weight. Coupled diblocks and soluble multiblocks according to the present invention are particularly useful for providing polymers in reduced viscosity applications according to the present invention or for producing star or comb polymers according to the present invention.

In certain aspects of the present invention which relates to reducing or preventing adhesion after surgery, preferred polymers for use in the present invention have the following characteristics: they are prepolymerized, chain-extended (in the case of triblocks), coupled (in the case of diblocks and some polymers), some polymers may be substantially non-crosslinked and biodegradable and/or bioabsorbable. In other aspects, the polymers may be crosslinked, especially where diblocks are used to produce star polymers. Preferred polymers may be reactive or non-reactive with animal, including human tissue. In general, preferred polymers according to the present invention do not produce an unintended or adverse tissue reaction. The present polymers are advantageously used as barrier materials to reduce or prevent adhesion as well as in numerous other applications including as coatings, sealants, lubricants, and in numerous non-medical applications. Polymers used in various preformed structures such as films according to the present invention are sufficiently flexible to enable the polymer to substantially conform to the surface of the tissue to be treated, yet at the same time have sufficient strength to function as an integral and therefore, effective barrier to allow suturing the material to tissue. Polymers used in other forms such as gels, dispersions, pastes and viscous solutions according to the present invention also have sufficient structural integrity to be delivered to a site within the body and prevent adhesions at the same time that the polymers are water soluble and/or water dispersible in order to be delivered.

In the present invention, PELA is the generic name used to denote certain preferred polymers which are used in anti-adhesion methods according to the present invention which comprise poly(ethylene oxide) and poly(lactic acid) blocks, which are chain extended with a diisocyanate, most preferably hexamethylene diisocyanate. PELA polymers are generally designated with respect to their composition by the average molecular weight of the poly(ethylene oxide) chain and by their (EO/LA) ratio, where EO is the number of ethylene oxide units present and LA is the total number of lactoyl units (ester units) present. A general definition of EO/LA ratio is presented hereinbelow.

In an anti-adhesion aspect of the present invention, the ACA triblock is preferably a substantially non-water soluble unit comprising poly(hydroxy acid) blocks and poly(oxyalkylene blocks), preferably poly($\alpha$-hydroxy acid) blocks and ethylene glycol, diethylene glycol and poly(ethylene oxide) chains or poly(ethylene oxide)-co-poly(propylene oxide) block copolymers. The A block of the ACA triblocks of the present polymers is biodegradable and ranges in size from one monomeric unit (a monomeric unit within the A block being considered lactic acid, glycolic acid or a related hydroxy acid (ester) unit even where lactide and/or glycolide or related reactants containing more than one hydroxyacid unit are used to produce the A block) up to about 400 or more monomeric units, with a preferred size ranging from about 4 to about 50 units, more preferably about 6 to about 30 units, even more preferably about 8 to about 16 monomeric units, which length depends upon the length or molecular weight of the C block combined with the A block in triblocks according to the present invention. It is to be noted that the size of the A block may well fall outside of the above range, depending upon the overall physical characteristics of the ACA triblock formed and the size of the C block.

The A block of AB diblocks and multiblocks according to the present invention ranges in size from one monomeric (ester) unit up to about 500 units or more, depending upon the application for the which the end product will be used. For those applications in which a low molecular is desirable (lower viscosity), the molecular weight of the A block will preferably be of a lower molecular weight, for example from one monomeric unit to about 20 monomeric units.

In ACA triblocks and AB diblocks according to the present invention which are used in an anti-adhesion method, the A block is derived preferably from an $\alpha$-hydroxy acid as described above, more preferably from units of glycolic acid, lactic acid (preferably L or D,L mixtures to promote bioabsorbability) or mixtures thereof, in the form of glycolide or lactide reactants (as explained in greater detail hereinbelow). In the final polymers to be used to reduce or prevent post-operative adhesion, the A blocks tend to create hard domains in the matrix and generally provide strength and structural integrity to the polymer. The A block is non-water soluble and is sized in combination preferably with the more water soluble/water dispersible B or C block in order to preferably promote phase separation between the A and C blocks in the ACA triblock and the final polymer to be used to prevent or reduce adhesions. Thus, the A block instills the final polymer with essential structural characteristics, which, in combination with the B or C block, results in a polymer which has excellent anti-adhesion characteristics (believed to be instilled by the B or C block) in combination with strength, structural integrity and biodegradability instilled by the A block. In addition, in certain embodiments according to the present invention, the length of the A block is believed to be important for providing a material with a phase separated microstructure.

In certain aspects of the present invention which relate to the treatment of adhesion, the B block (in the case of AB diblocks) and the C block (in the case of ACA triblocks) preferably comprises poly(ethylene oxide) or poly(ethylene oxide)-co-poly(propylene oxide) block copolymers and other PEO-rich chains which fall in the molecular weight ($M_w$) range as defined hereinbelow. The B or C block may preferably vary in size from about 100 Da (dalton units) up to about 200,000 Da or higher, with a more preferred range of about 400 Da up to about 20,000 Da. Even more preferably, the B or C block is a poly(ethylene oxide) ranging in size from about 400 to about 10,000 Da. Based upon the teachings of the present invention, one of ordinary skill will now know to vary the length of the B or C block and the A block to provide polymers having excellent anti-adhesion properties, depending upon the type of final formulation desired and its delivery characteristics.

In the anti-adhesion aspect according to the present invention, the ACA triblocks and AB diblocks (including some multiblocks) according to the present invention are described according to the length (number of monomeric repeating units) of the B or C block [preferably, poly(ethylene oxide), the repeating unit being in this case ethylene oxide units] divided by the total number of monomeric units in both A blocks (preferably, an $\alpha$-hydroxy acid such as lactic acid) of the ACA triblock or the A block of the AB diblock. This ratio is referred to as the EO/LA ratio. Polymers comprised of ACA triblocks or AB diblocks which are chain extended, coupled or crosslinked pursuant to the present invention also may be described in terms of an EO/LA ratio for the polymer, in which case the EO/LA ratio simply represents the ratio of oxyalkylene units to monomeric units in the entire polymer. The EO/LA ratio of the entire polymer may be determined by NMR analysis. These polymers may also be designated with respect to their composition by the average molecular weight of the poly(ethylene oxide) (PEG) chain or chains and by the weight percentage of the PEG chain or chains in the triblock, diblock or total polymer. It should be noted, however, that in instances where the chain extender, coupler or crosslinking agent comprises a poly(ethylene oxide) chain, the EO/LA ratio for the polymer may vary considerably from the EO/LA ratio found in the ACA triblock, AB diblock or multiblock (the total amount of EO may become considerably larger because of contribution of EO from the chain extender, and consequently, the EO/LA ratio for the polymer may be considerably larger than it is for the ACA triblock, AB diblock or multiblock). Likewise, the weight percentage of PEG found in such a polymer may also be quite different from that found in the ACA triblock or AB diblock.

Without being limited by way of presentation, the concept of the EO/LA ratio may be exemplified by a polymer described as a poly(ethylene oxide)-lactic acid block copolymer (PELA) 6,000/3.8, which is a hexamethylene diisocyanate chain extended ACA triblock copolymer comprising PEG chains having an average molecular weight of 6,000 and an EO/LA ratio of 3.8. The triblock in this polymer comprises, therefore, a 6,000 molecular weight PEG segment for the B block containing approximately 136 ethylene oxide units and two A blocks each containing, on average, approximately 18 LA units. Alternatively, the same polymer can be designated as 6,000/69.8%, where 6,000 is the average molecular weight of the PEG chains, and 69.8% is the weight percentage of PEG in the ACA triblock. For this PELA 6,000/3.8 polymer, the molecular weight of the triblock is approximately 8592 (6,000 for the PEG chain and two poly (lactic acid) A blocks each having a molecular weight of approximately 1296, for a total for the two A blocks of 2592). The weight percentage of the PEG block in this triblock is, accordingly, 69.8% (6,000/8592).

Alternatively, by way of example, the ACA triblock described above may be chain extended with, for example, the following chain extender: HDI-PEG4000-HDI, which is formed by reacting a poly(ethylene oxide) chain of molecular weight 4000 with two moles of hexamethylene diisocyanate. The repeating unit, after reaction of this chain extender with the ACA triblock described in the paragraph above is $[(LA)_{18}\text{-PEG6000-}(LA)_{18}\text{-HDI-PEG4000HDI-}]$. The molecular weight of the triblock 8592 (6000+2×18×72=2592) and that of the macrodiisocyanate chain extender is 2×168 (for the two HDI molecules)+4000 for the PEG chain. The MW of the repeating unit is therefore, 3592+4336=12928. The weight % of PEG in the repeating unit is 77.4% (6000+4000=10,000; 10,000/12928). In terms of the EO/LA ratio of the repeating unit, we have a total PEG MW of 10000, which comprises 10000/44 EO units=227.3 EO units. These units, divided by the 36 LA units present gives us a ratio of 6.3. Because it is difficult to define an average PEG MW in certain instances, since we could get, for the example above, an average MW of approximately 6000, which could be the result of PEG 10000 in the triblocks and 2000 in the chain extenders, or the result of simply having PEG chains of 6000 in each of the triblock and chain extender. The exemplary polymer we describe above is a PELA 6000/4000/77.4%.

The preferred EO/LA ratio for polymers which are used in the anti-adhesion aspect according to the present invention ranges from about 0.1 to about 100 or more, preferably about 0.5 to about 30, more preferably from about 0.5 to about 10.0, more preferably about 1.0 to about 5.0, more preferably about 1.5 to about 4.5, even more preferably about 2.5 to about 3.5 and most preferably about 3.0. In certain instances, the EO/LA ratio may fall outside of these ranges, depending upon the final characteristics of the polymers which are desired. Preferred EO/LA ratios for individual polymers may also vary according to the size of the B block and the type of chain-extender which is used. In certain embodiments, as the size (molecular weight) of the B block in the triblocks increases, the preferred EO/LA ratio will tend to be somewhat less than in triblocks and polymers where the size of the B block is less.

Tailoring the general properties of polymeric compositions according to the present invention is based upon choosing the individual components of the compositions in keeping with the application in which such composition is to be used, and the desired characteristics of the final composition, for example, the molecular weight of the composition, the form the final composition is to take, other physical properties of the composition, the biodegradability or bioerodability of the composition, the chemical or solubility characteristics of the composition e.g. the chemical requirements that enable the composition to be compatible with bioactive agents for controlled release delivery, etc. In the present invention, the use of the present polymers allows for improved physical characteristics compared to polymers which do not have the same type of chemistry.

Polymeric compositions according to the present invention may be changed or tailored to promote residence time and to enhance or delay the rate of biodegradation, to improve the physical/mechanical properties of solid and liquid polymers and in certain applications which utilize polymeric compositions in solution, to improve the rheological characteristics of the polymers. Because the chemistry of the present polymers may make use of a number of groups which may promote hydrogen bonding, the present polymers may also have greater interaction with, for example, tissue surfaces, proteins, and related molecules, cells and/or surfaces, a characteristic which may be advantageously employed in certain aspects of the present invention which relate to the use of the present polymers in biological and/or medical applications. In addition, increased hydrogen bonding may instill certain physical or mechanical characteristics to films according to the present invention, or alternatively, may improve the physical characteristics of liquid polymers or polymers in solution.

In the case of an anti-adhesion aspect according to the present invention, tailoring the properties of the anti-adhesion barriers generated by the present polymers is based upon combining (a) the enhanced anti-adhesion properties attributed, by way of theory, by the PEG (B block) segments; (b) the biodegradability of the polyester, preferably poly(hydroxy acid) A blocks; (c) the physical and/or mechanical properties derived from the partially phase separated microstructure of the polymeric matrix; and in certain instances, where relevant (d) the rheological characteristics of the various materials.

In certain aspects, the PEG (B block) content is related to the efficaciousness of the polymer as an anti-adhesion barrier. Higher PEG content may give rise to greater anti-adhesion activity, but with fast polymer degradation. Since there is a requirement for the barrier to stay in place separating the relevant tissues for a determined period of time, there is an optimal EO/LA ratio which combines maximum PEG content with the biologically required residence time. In agreement with these basic considerations, preliminary animal data indicate that polymers of the present invention comprising PEG chains of a 6,000 molecular weight and having an EO/LA ratio of approximately 1.0-3.0, preferably about 1.5 display optimal properties as anti-adhesion barriers.

Based upon the teachings of the present invention, one of ordinary skill in the art will now know to vary the length of the A block to the B block in a manner which provides polymers having excellent structural integrity, biodegradability and activity which substantially inhibits post-operative adhesion.

The polymers according to the present invention are pre-polymerized, chain-extended coupled and preferably attain high molecular weight. The polymers may be non-crosslinked or crosslinked. In order to increase the molecular weight of the polymers produced, the AB diblock (which may be end-capped with hydroxyl, amine or carboxylic acid groups) is chain-extended or coupled using difunctional compounds such as diisocyanate, dicarboxylic acid compounds or derivatives of dicarboxylic acids such as diacyl halides. The product which is formed from the reaction of the chain extender, coupling agent or crosslinking agent with the ACA triblock or AB diblock according to the present invention will depend upon the chemical nature of the nucleophilic (or electrophilic) moieties on the ACA triblock or AB diblock (or related multi diblocks) and the electrophilic (or nucleophilic) moieties on the chain extender, coupling agent or crosslinking agent. The reaction products can vary widely to produce different moieties, such as urethane groups, ester groups, urea groups and amide groups, among numerous others. For example, in the case of an ACA triblock or AB diblock which is hydroxyl terminated, reacting with diisocyanate chain extenders, produces a product containing urethane groups. In the case of amine groups terminating the ACA triblocks or AB diblocks reacted with diisocyanate chain extenders, the product contains urea groups. In the case of carboxylic acid groups terminating the ACA triblocks or AB diblocks (which can be converted to anhydrides or acyl halides) reacting with an amine terminated chain extender or crosslinking agent, the product contains amide groups. Alternatively, the reaction of a carboxylate-terminated triblock or diblock with an isocyanate also produces a product contains amide groups. Preferably, the nucleophilic end-capped triblocks to diblocks are chain-extended with diisocyanate compounds in order to produce chain-extended polymers according to the present invention, although the chemical approaches, as explained above, may vary greatly. In the case of structures such as films, the chain extenders are used to provide greater molecular weight to the triblocks, thus enhancing structural integrity. In the case of gels, liquid polymers and/or viscous solutions, the chain extenders, coupling agents or crosslinking agents may provide not only high molecular weight, viscosity control and structural integrity, but also a degree of water solubility/dispersibility consistent with the solubility and/or dispersibility of these polymers in water and the delivery of these polymers to a site within the patient's body. Thus, the chain extenders, coupling agents and crosslinkers may be used to provide a number of benefits hampering the beneficial morphological, mechanical and rheological effects.

The final polymers according to the present invention may be non-water soluble or in certain liquid, viscous solution and/or gel applications may absorb significant quantities of water. Certain polymers according to the present invention are water soluble, especially where the polymer has a high EO/LA ratio.

The polymers according to the present invention may be crosslinked in addition to being chain-extended or coupled. Crosslinking agents may be similar to the chain extenders and coupling agents used in the present invention, with the exception that the crosslinking agents contain at least three reactive functional groups, in contrast with chain extenders or coupling agents, which generally contain only two reactive functional groups. In the case of using crosslinking agents with diblock polymers, the resulting polymer may be a star-like or comb-like structure.

In addition to chain extenders, coupling agents and crosslinkers, end-capping agents, which contain only one functional group (i.e., they are monofunctional) may also be used in the present invention to end-cap triblocks, diblocks or multiblocks according to the present invention. By end-capping the polymers according to the present invention, the storage stability and shelf-life of the polymers increases significantly over polymers which are end-capped with reactive groups such as hydroxyl or amine groups.

DETAILED DESCRIPTION OF THE INVENTION

The following terms shall be used throughout the specification to describe the present invention.

The term "non-reactive" is used throughout the specification to describe compounds or portions of molecules (moieties) which do not participate in the reaction(s) to form an intermediate or polymer according to the present invention. Examples of non-reactive groups for use in the present invention include, for example, alkyl, aryl or aralkyl groups or substituted alkyl, aryl or aralkyl groups. It is noted here that most of the reactions to produce intermediates or polymers according to the present invention proceed through a heat initiated nucleophilic/electrophilic polymerization reaction as opposed to a radical initiated polymerization reaction. Consequently, those moieties which are preferably non-reactive fall within this definition. It is noted here that in certain instances, hydroxyethyl methacrylate (HEMA) or other —C=C— containing monomer or a group containing a blocking group (which can be removed to produce a reactive entity subsequent to intermediate or polymer formation) may also be used, for example, to initiate polymerization of monomers to produce an A block, or for inclusion in one or more other segments of triblocks, diblocks, multiblocks or polymers according to the present invention. Such a —C=C— containing moiety may be used in a subsequent coupling or crosslinking reaction to produce polymer compositions according to the present invention. Despite such reactivity in "radical polymerizable reactions", these monomers may be used in "non-reactive groups" according to the present invention. Non-reactive groups may also be "inert", i.e., they contain groups which are not reactive under any conditions. Examples of such inert non-reactive groups are alkyl groups, aralkyl groups or aryl groups, whether substituted or w-substituted, which do not contain blocking groups, —C=C— groups or other groups which can reactive further.

The term "diol" is used throughout the specification to describe any molecule or compound (such term including monomers, oligomers and polymers) containing two alcohol groups which can react with electrophilic groups (e.g., isocyanates, esters, acyl halides, activated esters, etc.) to produce compounds according to the present invention. Representative diols for use in the present include, for example, $C_2$ to $C_{24}$ (preferably, $C_2$ to $C_{12}$) diols, alkanols, aryl alcohols, aralkyl alcohols, substituted alkyl, substituted aryl and substituted aralkyl alcohols, including for example, ethylene glycol and butanediol, OH-terminated polycaprolactone and other OH-terminated polyesters and oligoesters, polyethers, such as poly(oxyalkylene) including poly(ethylene glycol), poly (propylene glycol), poly(ethylene glycol)-co-poly(propylene glycol) and other hydroxyl-containing compounds such as, for example, proteins, enzymes, growth factors, bioactive agents, polysaccharides and ACA triblocks, where A is a polyester unit and C is itself a diol, including a poly(oxyalkylene).

The term "diamine" is used throughout the specification to describe any molecule or compound (such term including monomers, oligomers and polymers) containing two amine groups (including primary and secondary amines, but preferably primary amines) which can react with electrophilic groups to produce compounds according to the present invention. Representative diamines for use in the present invention preferably include, for example, $C_2$ to $C_{24}$ (preferably, $C_2$ to $C_{12}$) diamines including alkyl amines, aryl amines, aralkyl amines, substituted alkyl, substituted aryl and substituted aralkyl amines, amino acids, oligopeptides and polypeptides, proteins, enzymes, bioactive agents. Lysine, oligolysine and polylysine may be used preferably as amino acids, oligopeptides and polypeptides in the present invention.

The term "dicarboxylic acid" is used throughout the specification to describe any molecule or compound (such term including monomers, oligomers and polymers) containing two carboxylic acid groups which can react with electrophilic groups or be converted to an electrophilic group such as an activated ester or acyl halide for reaction with nucleophilic groups to produce compounds according to the present invention. Representative dicarboxylic acids for use in the present invention preferably include, for example, $C_0$ to $C_{24}$ (more preferably, $C_0$ to $C_{12}$) dicarboxylic acids, including alkyl carboxylic acid, aryl carboxylic acid, aralkyl carboxylic acid, substituted alkyl, substituted aryl and substituted aralkyl carboxylic acid, including succinic acid, sebacic acid, adipic acid, malic acid, oxalic acid, maleic acid, fumaric acid, COOH-terminated polycaprolactone, and COOH-terminated polyesters or oligoesters.

The term "polymer" is used to describe compositions according to the present invention. Polymers according to the present invention may range in molecular weight (average molecular weight) from about 1,000-3,000 to several million or more and as described, include oligomers of relatively low molecular weight.

The terms "poly(ethylene glycol)", "poly(oxyethylene)" and poly(ethylene oxide) are used interchangeably to describe certain aspects of the present invention. These polymers, of varying weights, may be used in the B block of ACA triblocks and AB diblocks and multiblocks, thereof according to the present invention as well as in chain extenders, coupling agents and crosslinking agents which may also be used in the present invention. The terms "poly(oxyalkylene) containing" and "poly(ethylene oxide) containing" and are used to describe certain polymeric chains which contain at least some amount of poly(oxyalkylene) or poly(ethylene oxide). The terms "poly(oxyalkylene) rich" and "poly(ethylene oxide) rich" are used to describe certain polymeric chains containing at least 50% by weight (of the total weight of the polymeric chain described) poly(oxyalkylene) or poly(ethylene oxide).

The term "polyester" is used to describe polyester compounds found in A blocks of AB diblocks, multiblocks, or ACA triblocks or, although not present in diblocks, multiblocks or triblocks are nonetheless present in polymeric compositions according to the present invention where the "polyester" is a polymeric unit which may be derived from an aliphatic hydroxy carboxylic acid or a related ester, lactone, dimeric ester, carbonate, anhydride, dioxanone or related monomer and may be preferably derived from an aliphatic hydroxy carboxylic acid or related ester, such units derived from the following: including, for example, lactic acid, lactide, caprolactone, glycolic acid, glycolide, or a related aliphatic hydroxycarboxylic acid, ester (lactone), dimeric acid or related compound such as, for example, β-propiolactone, ε-caprolactone, δ-glutarolactone, δ-valerolactone, β-butyrolactone, pivalolactone, α,α-diethylpropiolactone, ethylene carbonate, trimethylene carbonate, γ-butyrolactone, p-dioxanone, 1,4-dioxepan-2-one, 3-methyl-1,4-dioxane-2,5-dione, 3,3,-dimethyl-1-4-dioxane-2,5-dione, cyclic esters of α-hydroxybutyric acid, α-hydroxyvaleric acid, α-hydroxyisovaleric acid, α-hydroxycaproic acid, α-hydroxy-α-ethylbutyric acid, α-hydroxyisocaproic acid, α-hydroxy-α-methyl valeric acid, α-hydroxyheptanoic acid, α-hydroxystearic acid, α-hydroxylignoceric acid, salicylic acid and mixtures, thereof. The use of α-hydroxyacids or related hydroxy acids and their corresponding cyclic dimeric esters, especially lactide, glycolide and caprolactone in the present invention, is preferred. It is noted that in using certain of the described monomers according to the present invention, the monomeric units which are produced are not specifically ester groups, but may include such groups as carbonate groups, urethane groups, anhydride groups and related groups which are derived from the above-described monomers. It will be understood that the term polyester shall encompass polymers which are derived from all of the above monomers, with those which actually produce ester units being preferred. Preferably, polyesters which are used in the present invention are biodegradable and/or bioabsorbable. The term "oligoester" is used to describe compounds which contain at least two ester groups (diester) to about 10 or more ester groups and are used in the present invention. Oligoesters tend to be shorter (have lower molecular weights) and contain fewer ester groups than polyesters.

The terms "poly(hydroxy carboxylic acid)" or "poly(α-hydroxy carboxylic acid)" are used to describe polyester A blocks of AB diblocks, ACA triblocks or multiblocks, thereof used in polymeric compositions according to the present invention where A is a polymeric polyester unit derived from an aliphatic hydroxy carboxylic acid or a related ester, dimeric ester or oligoester and is preferably derived from an aliphatic α-hydroxy carboxylic acid or related ester, including a cyclic dimeric ester, such as, for example, lactic acid, lactide, glycolic acid, glycolide, or a related aliphatic hydroxycarboxylic acid or ester (lactone) such as, for example, ε-caprolactone, δ-glutarolactone, δ-valerolactone, γ-butyrolactone and mixtures, thereof, among numerous others as set forth herein. The use of α-hydroxyacids and their corresponding cyclic dimeric esters, especially lactide and glycolide in the present invention, is preferred.

The term "diblock" is used to describe polymeric units which comprise an A block and a B block as described in general hereinabove. AB diblocks according to the present invention comprise a first polyester A block [preferably, a poly(hydroxy carboxylic acid)polyester] covalently linked to a B block which is comprised of a monofunctional amine, hydroxyl or carboxyl containing monomeric or polymeric compound, in certain aspects, preferably comprising poly(oxyalkylene) as described above. In the present invention, diblocks may be formed, for example, by initiating a polymerization of hydroxy carboxylic acid (or equivalent monomeric, dimeric or related building blocks) with a hydroxyl, amine or carboxyl-terminated compound block which is endcapped (on one end of the polymer) with a non-reactive group (for example, an alkyl, aryl or aralkyl group or substituted alkyl, aryl or aralkyl group, preferably, a $C_1$-$C_{12}$ alkyl group or an equivalent, or a protecting group which can be removed to provide a free nucleophilic moiety at a later time). The diblocks which are produced may then be further reacted with coupling reagents in a coupling reaction (preferably, in which the coupling agent and diblock are reacted in a 1:2 molar ratio), crosslinking agents and the like to produce polymers according to the present invention having favorable EO/LA ratios for use in reducing and/or preventing adhesion or for numerous other uses. Diblocks may be used in much the same way that ACA triblocks are used in the present invention, i.e., as building polymeric units of the polymers according to the present invention.

The term "di-diblock" is used to describe compounds according to the present invention which are produced by coupling (using a coupling agent) two AB diblocks pursuant to the present invention. The terms di-diblock and coupled di-blocks are used synonymously to describe the present invention. Di-diblocks according to the present invention may be represented by the general structure:

BA-W-AB, where W is derived from a simple diisocyanate or diacid (or related ester, activated ester or acyl halide), if B initiated polymerization to produce A using a hydroxyl or amine group (the A block has a terminal hydroxyl group to perform the coupling reaction in this case). Alternatively, W may be derived from a simple diisocyanate, or a diol or diamine, if B initiated polymerization of the A block using a carboxylate (carboxylic acid) as the initiating group.

The term "multi-diblock" is used to describe compounds which contain AB diblocks according to the present invention which have been linked through complex couplers to produce multiblocks according to the structure:

AB-V-BA, where V is a variety of more complex "couplers" which could be any one or more of the following:

an isocyanate or acid terminated triblock or other molecule (which may be monomeric, oligomeric or polymeric), if the polymerization of the A block is initiated using a hydroxyl or amine terminated B block (after polymerization, the A block is terminated with a hydroxyl group which can be used to perform the coupling reaction;

an isocyanate, amine or hydroxyl terminated triblock or molecule (which may be monomeric, oligomeric or polymeric), if the polymerization of A is initiated using a COOH-terminated B block (after polymerization, the A block is terminated with a COOH group to perform the coupling reaction).

The term "triblock" is used to describe polymeric units which are used in certain embodiments to produce the polymers according to the present invention which comprise a first polyester A block covalently linked to a diol, diamine or dicarboxylic acid compound C block (which block, in certain applications preferably includes poly(oxyalkylene) which is, in turn, covalently linked to a second polyester A block. Triblocks according to the present invention may be terminated by hydroxyl, amine, or carboxyl moieties, but in preferred embodiments, are terminated with hydroxyl groups which can be readily covalently linked to chain extenders, crosslinking agents or other groups which contain electrophilic moieties, to produce the final polymers which are used in the present invention. It is noted that the use of the term ACA to designate a triblock, in contrast to the term AB for a diblock is done to merely distinguish between the di-functionality of the C block of the ACA triblock and monofunctionality of the B block of the diblock. Whereas the C block is derived from a difunctional diol, diamine or dicarboxylic acid molecule, the B block by design (other than in cases where the B block contains for example, a blocking group or a —C=C— group, which may participate in additional reactions after an intermediate or polymer is first synthesized) is monofunctional (i.e., is derived from a compound containing only one hydroxyl, amine or carboxylic acid moiety which participates in a reaction to initiate the polymerization of or bond to an A block).

The term "star-like molecule" or "star polymer" is used throughout the specification to refer to a type of molecule which is star-like in character. This type of compound may be made by using a tri- or higher function B block (e.g. an oligopeptide with at least three amine groups) such that each functional group initiates the formation of an A block. Without further modification, the resulting product is a star polymer. Alternatively, if AB diblocks are reacted with higher functional crosslinking agents or the formation of the A block is initiated with a tri- or polyfunctional agent, such as trimethylolpropane, the result will also be a star polymer. If we start with a polyfunctional agent, for example, polyHEMA, or other polyfunctional molecule such a poly acrylic acid to initiate the A block polymerization, the result would be a star or "comb" polymer, if the A block was simply generated. If the A blocks are coupled, the result would be crosslinked materials.

The term "non-water soluble" or "substantially non-water soluble" is used to describe certain preferred ACA triblocks or AB diblocks used in various forms according to the present invention. In the present invention, in forms such as viscous solutions, gels, pastes or emulsions in which the polymers are substantially water soluble, the AB diblocks, AB multiblocks or ACA triblocks may be water soluble or non-water soluble. Non-water soluble diblocks or triblocks according to the present invention are soluble in water up to a limit of no more than about 0.5-0.6 g per 100 ml of water, preferably less than about 0.2 g per 100 ml of water. In determining water solubility, diblocks or triblocks according to the present invention are dissolved in, agitated or mixed in water at room temperature (i.e., at a temperature of about 20-23° C.) for a period of two hours. It is noted that in the present invention, chain extended triblocks which are used to produce structures such as films according to the present invention are also preferably substantially non-water soluble, i.e, they are limited in water solubility to no more than about 0.2 mg/ml. This limitation of water solubility reflects the fact that in certain embodiments according to the present invention which relate to the anti-adhesion aspect of the present invention, substantially non-soluble triblocks or diblocks which are preferably used in the present invention comprise at least about 25-30% by weight of A blocks.

An amount of the A blocks in the AB diblocks or ACA triblocks comprising at least about 25-30% by weight generally renders the triblocks or diblocks according to the present invention substantially non-water soluble. It is to be noted that water solubility or the absence of water solubility of the triblocks or diblocks may depend upon the molecular weight of the material. This characteristic is advantageous in the present polymeric compositions because the length and/or size of the A block instills structural integrity and biodegradability to the final polymer, but also, by virtue of the relative hydrophobicity of the block, tends to reduce the water solubility of the AB diblock or ACA triblock. Consequently, polymeric compositions according to the present invention which contain a proper balance of A block or blocks to B block have a slow rate of biodegradability and consequently, a longer period of interaction with tissue to be protected from adhesion formation. In aspects according to the present invention which utilize a B block which contains (poly)ethylene oxide, this is reflected overall in the EO/LA ratio of the polymers according to the present invention.

Polymers to be used in viscous solutions, dispersions and/or gels according to the present invention are preferably water soluble and/or water dispersible and may use many of the same or similar AB diblocks or ACA triblocks used in polymeric structures such as films according to the present invention. In certain applications of the present invention in an anti-adhesion method, in particular, in producing a liquid version which is substantially non-water soluble, having acceptable viscosity and flow characteristics for favorable administration, the polymers are actually substantially non-water soluble. Consequently, in applications such as films as well as in certain embodiments of the gel, dispersion and viscous solution applications, regardless of the way the polymers are administered, the ACA triblocks or AB diblocks which are preferably used are substantially non-water soluble. In certain alternative embodiments of the gels, dispersions and viscous solutions of the present invention, especially where the polymers are to be readily water dispersible, water solubility of the AB diblocks or ACA triblocks may be an advantageous characteristic, in which case, the inclusion of A blocks which comprise as little as about 1-5% by weight of the AB diblock or ACA triblock may be useful in the present invention.

The term "storage stable" is used to describe polymeric compositions according to the present invention in solid, liquid, gel or related forms. Polymeric compositions which are end-capped with non-reactive groups (i.e., cannot further participate in a reaction) tend to be significantly more stable than polymers which are end-capped with reactive groups, particularly hydroxyl, amine or carboxylic acid groups. In the present polymers, the non-reactive groups which cannot further participate in reactions such as transesterification or transamidation reactions, where the polymer may change in chemical and/or physical character over time, and consequently are preferably long-term storage stable, i.e., stable for a period of at least one month, preferably at least 6 months, a year or even longer, are preferred. Storage stable polymer compositions according to the present invention may also more easily comply with quality control.

The term "adhesion" is used to describe abnormal attachments between tissues or organs or between tissues and implants (prosthetic devices) which form after an inflammatory stimulus, most commonly surgery, and in most instances produce considerable pain and discomfort. When adhesions affect normal tissue function, they are considered a complication of surgery. These tissue linkages often occur between two surfaces of tissue during the initial phases of post-operative repair or part of the healing process. Adhesions are fibrous structures that connect tissues or organs which are not normally joined. Common post-operative adhesions to which the present invention is directed include, for example, intraperitoneal or intraabdominal adhesions and pelvic adhesions. The term adhesion is also used with reference to all types of surgery including, for example, musculoskeletal surgery, abdominal surgery, gynecological surgery, ophthalmic, orthopedic, central nervous system, cardiovascular and intrauterine repair. Adhesions may produce bowel obstruction or intestinal loops following abdominal surgery, infertility following gynecological surgery as a result of adhesions forming between pelvic structures, restricted limb motion (tendon adhesions) following musculoskeletal surgery, cardiovascular complications including impairing the normal movement of the heart following cardiac surgery, an increase in intracranial bleeding, infection and cerebrospinal fluid leakage and pain following many surgeries, especially including spinal surgery which produces low back pain, leg pain and sphincter disturbance.

The term "EO/LA ratio" is used to describe the relative amount of poly(ethylene oxide) or poly(ethylene oxide)-co-poly(propylene oxide) and ester units (such term including monomeric units which are not technically ester units, as described in greater detail herein but preferably, are hydroxy carboxylic acid units, even more preferably, α-hydroxy carboxylic acid units and most preferably, lactic acid units) which are used in AB diblock or ACA triblock copolymers and chain-extended or coupled polymers according to the present invention. This term refers to the length (number of monomeric units) of the B or C block [preferably, poly(ethylene oxide), the monomeric units being ethylene oxide units] divided by the total number of hydroxy acid (ester) units in both A blocks (preferably, lactic acid) of the ACA triblock or in the A block of the AB diblock as described hereinabove. Polymers comprised of AB diblocks or ACA triblocks which contain significant (poly) ethylene oxide (in B or C blocks or in other components of the present composition) which are chain extended pursuant to the present invention are also described in terms of an EO/LA ratio. The EO/LA ratio for preferred polymers for use in the anti-adhesion aspect according to the present invention generally ranges from about 0.1 to about 100 or more, preferably ranges from about 0.5 to about 30 or more, more preferably from about 0.5 to about 10.0, more preferably about 1.0 to about 5.0, more preferably about 1.5 to about 4.5, even more preferably about 2.5 to about 3.5 and most preferably about 3.0. In certain instances, the EO/LA ratio may fall outside of these ranges, depending upon the final characteristics of the polymers which are desired and the application for which the polymer is used. In the case of polymeric films to be utilized in anti-adhesion aspects according to the present invention, the EO/LA ratio preferably ranges from about 0.1 to about 25 or more, more preferably about 0.5 to about 10, even more preferably about 1.0 to 5.0, even more preferably about 1.5 to about 4.5 and even more preferably about 2.5 to 3.5, with about 3.0 within this range being particularly preferred. In the case of viscous solutions, dispersions and/or gels which are utilized in the anti-adhesion aspect, the polymers may contain EO/LA ratios which range up to 30 or more. It is noted that in the case where a hydrophobic unit is used in the B or C block (for example a propylene oxide unit or higher alkylene oxide unit, this unit is considered as being a component in the denominator (LA) of the EO/LA ratio.

The term "prepolymerized" is used to describe the polymers according to the present invention which have been completely reacted before being introduced or administered in an application, for example, to a patient to be treated. Prepolymerized polymers according to the present invention stand in contrast to polymers which may be polymerized in situ, i.e., at the site of administration in the patient. Prepolymerized polymers of the present invention are utilized to create both preformed structures, e.g., compositions having three-dimensional structure such as films, cylinders, spheres, rods, blocks, tubes, beads, foam or rings, etc. and related structures, and non-preformed compositions such as sprays, gels, liquid polymers, pastes, viscous solutions and dispersions, among others.

The term "crosslinked" or "crosslinker" is used to describe agents which covalently bond the ACA triblocks or AB diblocks to other triblocks, diblocks or other moieties in the present polymers. As used herein, a crosslinker refers to a chemical compound which contains at least three (3) reactive moieties, for example, nucleophilic and/or electrophilic moieties, or moieties such as double-bonds, which can react through a radical initiated mechanism. In preferred embodiments, crosslinking agents according to the present invention have at least three of the same type of moieties, for example nucleophilic, electrophilic or radical-initiated moieties in order to facilitate the reaction of the crosslinker with triblocks and diblocks according to the present invention. In many respects, crosslinking agents are related to chain-extending agents in the present invention except that chain-extending agents contain only two reactive moieties, whereas crosslinking agents contain at least three reactive moieties. Exemplary crosslinking agents which can be used in the present invention include those which contain at least three isocyanate moieties, for example, isocyanurate, among numerous others, or a mixture of reactive moieties, such as carboxylic acid and hydroxylic groups (an example being citric acid or tartaric acid, among numerous others) and amine groups. One of ordinary skill in the art will be able to readily determine the type and amount of crosslinking agent which may be used in the present invention in order to facilitate the therapeutic method according to the present invention and the delivery of the polymers to a treatment site in a patient.

In the present invention, reaction of an AB diblock with a crosslinking agent may produce a star molecule or, in other instances, different structures such as a comb polymer, for example, but not a crosslinked system per se. Inasmuch as the AB diblock will generally contain only one reactive moiety per molecule (except in the case where one of the two blocks contains a blocking group which may be removed and then reacted subsequent to the initial formation of the AB diblock), the use of crosslinkers will produce predetermined structures such as star or comb molecules. The inclusion or incorporation of an additional moiety in the diblock to which a crosslinking agent can react will generate a more elaborate crosslinked system akin to that produced with the ACA triblocks of the present invention.

The term "non-crosslinked", "substantially non-crosslinked", "crosslinked" or "substantially crosslinked" are used to describe the polymers according to the present invention which exhibit or display a substantial absence of crosslinking or, in other embodiments, substantial crosslinking. Polymers according to the present invention are advantageously associated with substantial post-surgical adhesion prevention or reduction as well as numerous other applications. In certain embodiments, the present polymers actually prevent adhesions. Polymers according to the present invention which are considered substantially non-crosslinked preferably contain less than about 1.0% crosslinking, more preferably less than about 0.5% by weight crosslinking, even more preferably less than about 0.1% by weight crosslinking, most preferably less than about 0.05% by weight crosslinking are advantageously employed in the present invention. As used herein, reference to 1.0%, 0.5%, 0.1% etc. crosslinking refers to the amount by weight of a crosslinker which may be found in the polymers of the present invention. In other embodiments, polymers may be crosslinked, i.e., they may contain substantially more crosslinking agent than 1.0% by weight crosslinking agent.

The polymeric compositions according to the present invention may be chain-extended or coupled rather than crosslinked, but may be crosslinked in addition to being chain extended or coupled. It is also possible to produce crosslinked, non-chain extended polymers according to the present invention, but these polymers, if used in anti-adhesion aspects of the present invention, are preferably crosslinked with more hydrophilic chain extenders in order to maintain a favorable EO/LA ratio. In certain preferred embodiments, the polymers may be both chain extended and crosslinked. In the present compositions, chain extension provides the type of structural integrity and uniformity associated with the exceptional performance of the polymers of the present invention as anti-adhesion barriers. While not being limited by way of theory, it is believed that chain extension alone or in combination with crosslinking, in contrast to mere crosslinking with hydrophobic chain extenders without chain extension, allows a degree of mobility and flexibility of the hydrophilic B block which is consistent with anti-adhesion activity. In the anti-adhesion aspect of the present invention, the polymeric compositions according to the present invention provide an environment in which the A blocks (of the ACA triblock or AB diblock) will form hydrophobic, and often partially crystalline, hard microphases of high structural integrity and the B or C blocks will form hydrophilic, flexible phases, which are believed to be primarily responsible for good anti-adhesion activity. The formation of this microstructure, which is believed to be associated with polymeric compositions according to this invention and in particular, the flexibility of the PEG B or C blocks where used, produces excellent barriers for the reduction or prevention of post-surgical adhesions. Hydrophobic crosslinking of the triblocks according to the present invention without chain-extension (in contrast to hydrophilic crosslinking which may be used advantageously) not only limits molecular mobility, of special importance being its effect on the PEG segments, but also hampers or in certain instances, is believed to prevent microphase segregation from taking place. These two phenomena are believed to be associated with the production of less successful anti-adhesion barriers.

In certain polymers according to the present invention which are used in the anti-adhesion aspect according to the present invention, crosslinking, especially if crosslinking density is high, prevents or at least substantially limits phase separation and to a greater extent, crystallization. In the present invention, the limitation of phase separation and crystallization will depend on the crosslinking density which is a function not only of the number of trimers which are crosslinked to those which are chain extended, but also on the molecular weight of the diblock or triblock and MW weight of its different components. In addition, the degree to which crosslinking will limit phase separation (and also crystallization) will depend on the molecular weight and flexibility of the crosslinker. Clearly, the shorter the crosslinker, the greater the decrease in molecular mobility and therefore, phase separation. The effect of the crosslinker being hydrophobic or hydrophilic on phase separation and molecular or segmental mobility is two-fold: a) hydration will render the crosslinker more flexible and b) if the crosslinker is crystalline, its crystallinity will be destroyed by hydration. One is therefore, not limited to relatively low molecular weights of the crosslinker where, due to perturbations of the short chain, the polymer is unable to crystallize.

The term "coupler" is used to describe a difunctional compound which couples two AB diblocks together to produce coupled di-diblocks or multi-blocks according to the present invention. Couplers and chain-extenders are similar compounds, but a coupler is a difunctional compound which couples two diblocks together, whereas a chain-extender is used to extend the ACA triblocks into very high molecular weight polymeric chains.

As used in the present invention, the AB diblocks or ACA triblocks used in the present polymers are preferably chain extended or coupled. The chain extenders or couplers which are used are difunctional compounds (nucleophilic or electrophilic) which react with the end-cap reactive group of the diblocks or triblocks to produce di-diblocks, multiblocks or chain extended triblocks according to the present invention. Electrophilic couplers include, for example, diisocyanates, diacids, diesters, active diesters and acyl halides (all of which may be derived from dicarboxylic acids), among others, and nucleophilic couplers, which may include diols, diamines (as otherwise described herein) and hydroxyl amines. Electrophilic couplers are useful for coupling hydroxyl or amine-capped diblocks or triblocks, the resulting products containing urethane groups, urea groups (from the diisocyanate) and ester groups or amide groups (from the diacids, diesters, or related coupling agents). In addition, diisocyanates are useful for coupling or chain-extending diblocks or triblocks which are capped with carboxylic groups, such coupling reaction resulting in the formation of an amide group. Nucleophilic couplers such as diols and diamine are useful for coupling diblocks or triblocks which are end-capped with carboxyl groups, the resulting products containing ester groups or amide groups. Couplers may be simple, e.g., a simple monomeric compound containing two functional groups, or complex, e.g., containing oligomeric or polymeric moieties such as polyesters or polyethers, or may be based upon the reaction of a number of coupling agents to such as diols or diamines and diisocyanates or diacids, etc. to produce complex coupling agents.

In the present invention, the amount of coupling agent or chain extender which is included within the polymers according to the present invention may vary. In the case of polymers which incorporate an ACA trimer, the molar ratio of chain extender or coupler to ACA triblock in the present polymers varies from about 1.25 to about 2:1, more preferably about 1.5:1 to about 2:1, most preferably about 2:1. In the case of AB diblocks, the coupler is used preferably in a molar ratio of about 2:1 (AB diblock to coupler) in order that virtually all or nearly all of the functional groups on the end of the diblock are reacted with coupling agent.

In the case of diblocks, the preferred molar ratio of coupling agent to AB diblock varies from about 0.25 to about 1.0, with a more preferred ratio of about 0.5 to 1.0. When used with diblocks, the couplers form a di-diblock. It is noted that in synthesizing the present chain-extended polymers, the amount of chain extender which is reacted with AB diblock or ACA triblock to produce compositions according to the present invention is generally slightly higher than the amount which is expected to be included in the final synthesized polymers.

Chain extenders or couplers which are used in the present invention, preferably contain no more than about 1% by weight of a crosslinking compound (such term signifying a compound containing at least 3 functional groups which can react with the end-cap group of the triblock and which generally appear in a chain extender sample as a side product of the synthesis or production of the chain extender), more preferably, less than about 0.5% by weight of a trifunctional compound and even more preferably less than 0.1% by weight. In certain embodiments, it is preferable to employ a difunctional chain extender which contains as little trifunctional (or higher functionality) compound as is practical. Also, the occurrence of side reactions which would lead to crosslinking of the polymers is negligible, due to both compositional as well as experimental parameters of the synthesis of the polymers of the present invention. Of course, in certain embodiments which separately employ crosslinking agents (either alone or in addition to chain extenders), the inclusion of weight percentages of crosslinking agents outside of the above-described weight ranges is within the scope of the present invention.

In the case of polymers which are used in structures such as films, the chain extenders are preferably non-water soluble. In the case of polymers which are used in systems such as water soluble gels, dispersions or viscous solutions, the chain-extenders are preferably highly water soluble. Preferred water soluble chain-extenders include, for example, polyethylene glycol diisocyanates or poly(ethylene oxide)-co-poly(propylene oxide) copolymer diisocyanates, with the polyethylene glycol or poly(ethylene oxide)-co-poly(propylene oxide) copolymer chain ranging in molecular weight from about 200 to about 20,000 or more with a preferred molecular weight ranging from about 600 to about 15,000, even more preferably about 600 to about 10,000. In cases where the preferred embodiment is a non-water soluble polymer in a liquid form, the chain extenders may also be substantially non-water soluble. The role of the chain extenders in the gels and/or viscous solutions according to the present invention is to promote the water solubility/dispersibility of the polymers and affect their viscosity in an effort to provide polymers which are readily deliverable to a site in a patient's body and also to fine tune the kinetics of degradation, the dilution and/or the solubilization of these polymers, to obtain optimal residence time and enhance the performance of the polymer as a barrier between tissue planes.

As an advantageous feature of the present invention, certain preferred polymers of the present invention are employed in the present invention to substantially reduce or prevent adhesions. While not being limited by way of theory it is believed that the polymers according to the present invention which have a favorable EO/LA ratio allow greater mobility of polyoxyalkylene blocks (and in particular, polyethylene oxide blocks) within the AB diblock or ACA triblocks used in the present invention, a condition which is believed to at least partially explain the favorable results obtained by the present polymers in substantially reducing or preventing adhesions. Chain extended polymers according to the present invention are more likely to enhance phase separation of the distinct A and B blocks which comprise the triblocks, a condition which is associated with the superior performance of the polymers of this invention as anti-adhesion barriers. It is preferred that the polymers of the present invention should be chain extended and substantially non-crosslinked, or chain extended and crosslinked while maintaining a favorable EO/LA ratio of the entire polymer as well as preserving flexibility and segmental mobility, as much as possible. Polymers which are simply crosslinked (without chain extension) are also useful in the present invention, provided that the crosslinking agent is substantially hydrophilic in composition and allows the retention of the required degree of flexibility and segmental mobility.

The term "integral" is used to describe polymers according to the present invention which are substantially non-permeable to mesenchymal cells, platelets, blood cells and other cells which are involved in the biology of adhesion formation. Integral polymers preclude cells which are involved in the adhesion process from crossing the polymer barrier and initiating the adhesion process. Integral polymers also exhibit favorable physical characteristics and mechanical properties consistent with substantially reducing or eliminating adhesions.

The term "coupled" or "chain-extended" is used to describe polymers according to the present invention wherein the basic diblock or triblock is reacted with a difunctional (preferably, containing two electrophilic groups such as isocyanates, activated esters and acyl halides, among others, but also possibly containing two nucleophilic groups such as alcohols, amines and carboxylates) chain extender to increase the molecular weight of the present polymers. Preferred chain extenders or couplers for use in the present invention include, for example, diisocyanates, activated esters or acyl halides, but may include diols, diamines, dicarboxylates and hydroxylamines, among others. In certain preferred embodiments, especially in the form of films, the present polymers may be substantially non-crosslinked and are instead, chain-extended to provide sufficiently high molecular weight polymer chains to enhance the strength and integrity of the final polymer film compositions as well as affecting the rate of degradation. It is noted that chain extension of the polymers provides adequate strength and integrity of the final films and other structures, yet allows a degree of motility of the individual polyoxyalkylene B blocks within the ACA triblock or AB diblock in order to maximize the adhesion inhibiting characteristics of the films. In contrast, hydrophobically crosslinked polymers which are not chain extended, provide a more rigid structure which may limit movement of the individual polymeric blocks.

Preferred chain extenders or couplers for use in the present invention include diisocyanates of the general formula:

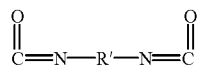

where R' is a $C_2$ to $C_{12}$, preferably a $C_2$ to $C_8$ alkylene group, a cycloalkyl or cycloalkyl-containing group, an aryl or aryl-containing group, 4,4'-diphenylmethane, toluene, naphthalene, 4,4'-dicyclohexylmethane, cyclohexyl, 3,3'-dimethylphenyl, 3,3'-dimethyl-diphenylmethane, 4,6'-xylylene, 3,5,5-trimethylcyclohexyl, 2,2,4-trimethylhexamethylene or p-phenylene. Equivalents of diisocyanates may also be used as chain extenders in the present invention. Additional chain extenders may include macrodiisocyanates including isocyanate terminated poly(oxyalkylene) including isocyanate terminated polymers comprising poly(ethylene oxide) and polyethylene oxide)-co-poly(propylene oxide), among others.

Additional preferred chain extenders for use in the present invention include, for example, those according to the formula:

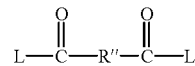

where R" is a $C_0$ to $C_{12}$, preferably a $C_2$ to $C_8$, alkylene group or a hydroxyl or carboxylic acid substituted alkylene group, alkene, a cycloalkyl, hydroxyl or carboxylic acid-containing cycloalkyl or cycloalkyl-containing group, an aryl or aryl-containing group or a polyoxyalkylene chain comprised of poly(ethylene oxide), poly(ethylene oxide)-co-poly(propylene oxide) or other poly(ethylene oxide) rich chains and L is hydroxyl, a halide such as Cl, I or Br or an ester group which can be prepared from a hydroxyl group such as an alkyl, phenyl, benzyl or substituted alkyl, phenyl or benzyl group, including activated ester groups such as a tosyl group, mesyl group or related activating groups.

The moiety

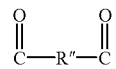

may be derived from numerous di- and tricarboxylic acids including, for example, citric acid, malic acid and tartaric acid, among numerous others such as oxalic acid, malonic acid, succinic acid, 2,3-dimethylsuccinic acid, glutaric acid, 3,3-dimethylglutaric acid, 3,3-dimethylglutaric acid, 3-methyladipic acid, adipic acid, pimelic acid, suberic acid, azelaic acid, sebacic acid, 1,9-nonanedicarboxylic acid, 1,10-decanedicarboxylic acid, 1,1-undecanedicarboxylic acid, 1,12-dodecanedicarboxylic acid, maleic acid, fumaric acid, diglycolic acid, hydromuconic acid, among others, including equivalents of these acids. These di- and tricarboxylic acids may be used to chain extend or couple the AB diblocks or ACA triblocks under controlled conditions so that crosslinking is substantially prevented. Alternatively, the use of the tricarboxylic acids may result in substantial crosslinking in certain aspects of the present invention. In the case of using dicarboxylic acids containing additional carboxylic acid groups and/or other polar groups such as hydroxyl groups, as in the case of citric acid or malic acid, among others, these will tend to enhance the water solubility of the final polymeric compositions.

The term "biodegradable" relates to the characteristic whereby a polymer will degrade. Preferred polymers according to present invention are biodegradable. Preferred polymers according to the present invention which are utilized in vivo readily degrade in vivo and breakdown readily into monomeric units such as hydroxy acids. In the case of the use of PEG chains (B or C blocks) with polymers which are utilized within the body, although these chains are not biodegradable, they are readily excreted by the patient upon degradation of the A block. The degradation of the present polymers mainly takes place through the hydrolysis of reactive bonds in the A block, such as aliphatic esters. The hydrolysis reaction is generally dependent upon pH. The rate constant for hydrolysis tends to be much higher at high pH (greater than 9.0) and low pH (less than 3.0) than at neutral pH (6.0 to 8.0). The rate constant for hydrolysis tends to be higher under basic conditions than under acidic conditions.

The A blocks of the diblocks and triblocks of the present polymers tend to be biodegradable, whereas the B or C blocks of the triblocks, diblocks and chain extenders tend not to be biodegradable. In the case of water-soluble chain extenders and crosslinking agents which are preferably utilized in gels and viscous solutions according to the present invention, these chain extenders and crosslinking agents, which generally are highly water soluble, tend not to be biodegradable. In addition, when using polymers containing A blocks derived from α-hydroxy acids, the polymeric A blocks will degrade to individual α-hydroxy acids which are biosynthetically useful and may be involved in the patient's "biochemistry". In contrast, however, although the poly(oxyalkylene) polymeric B or C blocks are biocompatible, they are neither biodegradable nor bioabsorbable. Thus, in using the polymers according to the present invention it is recognized that the poly(oxyalkylene) blocks will remain as polymeric units in vivo until such time as the blocks are excreted. Consequently, the choice of an upper molecular weight range of the polyoxyalkylene block in the polymers according to the present invention which are to be used in vivo will very much depend on the ability of the body to excrete or otherwise rid the body of the material.

The term "strength", "mechanical strength" or "sufficient suture-holding ability" describes favorable mechanical and/or physical characteristics of the present polymers and reflects the fact that preferred polymers for use in the present invention (generally, as films) having a mechanical strength which is sufficient to allow a suture to be used to anchor the polymer to a tissue site without appreciable tearing or ripping of the film. These preferred polymers according to the present invention have an Ultimate Tensile Strength value preferably within the range of about 5-35 MPa and Elongation at Break values generally within the range of about 400-2000%.

The term "flexible" is used with respect to a physical description of the polymers of the present invention to reflect the fact that the present polymers are essentially non-rigid and non-brittle, and generally display an elastomeric behavior and tend to be conformable to a tissue surface to be treated. That is, the present polymers contain sufficient flexibility and are pliable enough to substantially conform to the contours of the tissue surfaces to be treated. Thus, polymeric compositions according to the present invention have a Young's Modulus preferably within the range of about 50-150 MPa.

The term "homogeneous" is used to describe preferred polymers according to the present invention. The term homogeneous is associated with the inclusion in the final polymer compositions of a population of diblocks and triblocks which are generally of the same size and preferably have a polydispersity of between about 1.0 and 2.0, more preferably about 1.1 to about 1.5 and even more preferably about 1.1 to about 1.2. Homogeneous triblocks and diblocks are associated with reproducible mechanical and physical characteristics and favorably consistent biodegradability.

The term "structure" is used to describe polymers according to the present invention which have form, size and dimensions which are established outside the body and will not significantly change upon being placed inside the body of the patient to be treated. The term structure embraces not only flat surfaced structures (i.e., films) in the traditional manner, but also cylinders, tubes and other three dimensional structures which are not substantially changed by the anatomy of the patient into which the structure has been placed.

The term "gels" is used to describe dispersions or suspensions of polymer which have been formed by dissolving, suspending or dispersing polymer in an aqueous solution for delivery to a site within the patient's body in order to prevent adhesions. Gels of the present invention typically contain polymer in a sterile aqueous solution (such solution comprising saline solution, sterile water or a water/ethanol mixture) at a viscosity ranging from about 100 to about 150,000 or more, preferably about 500 centipoise units up to about 50,000 centipoise units or more. More preferably, the gels are delivered in sterile, isotonic saline solution at a viscosity ranging from about 2000 centipoise units up to about 30,000 centipoise units depending upon the application. In certain aspects according to the present invention, liquid polymeric compositions comprising non-water soluble polymers may also be used.

Gels according to the present invention may be used in numerous applications to reduce or prevent adhesions, but preferably are employed to reduce or prevent adhesions following general surgical procedures and related surgeries which are minimally invasive. Gels may utilize non-water soluble ACA triblocks which are chain extended with water-soluble or hydrophilic chain extenders in order to render the overall polymeric composition water dispersible or water soluble. AB diblocks may also be used in this gel aspect according to the present invention without limitation. Certain phases within the gel polymer compositions will be advantageously non-water soluble in order to promote the structural integrity and reduce the overall rate of biodegradability of the gel formulations in the body.

The term "viscous solution or suspension" is used to describe free-flowing solutions or suspensions of polymers according to the present invention wherein the solution has a viscosity which is greater than about 1 centipoise unit and less than about 60,000 or more centipoise units, more preferably about 1000 centipoise units to about 40,000 centipoise units or more, even more preferably about 2,000 centipoise units to about 20,000 centipoise units and above within this range. Viscous solutions or suspensions, of polymers according to the present invention at viscosities approaching the high end of the range of viscosities may be indistinguishable from gels at the low end of a viscosity range. The present invention also contemplates liquid polymeric compositions having appropriate viscosity and flow characteristics and their use to reduce and/or prevent adhesions.

In the anti-adhesion aspect of the present invention, the AB diblock or ACA triblock is a unit which is preferably comprised of ester units derived from a variety of monomers as described hereinabove and preferably comprises poly(hydroxy acid) polymers in the A block and poly(oxyalkylene) polymers in the B or C block. The A block is however, substantially biodegradable and ranges in size from one monomeric unit up to about 400 or more monomeric units, with a preferred size ranging from about 4 to about 50 units, more preferably about 6 to about 30 units, even more preferably about 8 to 16 units. In this aspect of the present invention, the A block preferably is derived from an alpha-hydroxy acid or a related ester or lactone which produces monomer units of alpha-hydroxy acid within the polymeric chain as will be described in greater detail below. More preferably, the A block is derived from units of glycolic acid, lactic acid or mixtures thereof, in the form of glycolide or lactide reactants (dimeric α-hydroxy acids as explained in greater detail hereinbelow). In this anti-adhesion aspect of the present invention, the B or C block preferably comprises poly(ethylene oxide) or poly(ethylene oxide)-co-poly(propyleneoxide) block copolymers. In certain aspects of the present invention, for example, where a polymer comprises a sufficient weight percent of poly(ethylene oxide) units in chain extenders and/or crosslinking agents to instill the overall polymer with a favorable EO/LA ratio, the B or C block may be hydrophobic or hydrophilic and derived from, for example, diols, diamines and dicarboxylic acids, among other equivalent compounds.

In certain preferred aspects according to the present invention, for example, where the polymer is used in an anti-adhesion application in vivo, examples of diol, diamine and dicarboxylic acid compounds which may be used in the present invention include, for example, OH-terminated diol molecules such as ethylene glycol, butanediol (generally a $C_2$ to $C_{12}$ unsubstituted or substituted, saturated or unsaturated, preferably a saturated, linear diol), OH-terminated polycaprolactone chains ranging in molecular weight from several hundred up to several thousand or more (4,000+), polypropylene glycol) also ranging in molecular weight from several hundred to several thousand or more (4000+), OH-terminated polyesters or oligoesters such as OH-terminated poly(ethylene succinate) or poly(hexamethyleneadipate) or polyfunctional diols such as tartaric acid (containing two OH groups which are reactive with isocyanates and two carboxylic acid groups, which, in carboxylate form, will function to enhance the overall hydrophilicity of the composition and can serve to provide a material with pH dependent water solubility). Additional examples of such compounds include amine-containing compounds (preferably, a $C_2$ to $C_{12}$ diamine) such as ethylene diamine, hexamethylene diamine, amino acids, such as lysine (where two amine groups react leaving an unreacted carboxylic acid group) and oligopeptides (such term including compounds containing from one to 100 peptide units) with two reactive amino groups, among numerous others. Examples of difunctional carboxylic acid-containing compounds include, for example any $C_2$ to $C_{24}$, preferably a $C_2$ to $C_{12}$, saturated or unsaturated dicarboxylic acid, including succinic acid, sebacic acid, among numerous others, including adipic acid, succinic acid, malic acid, or fumaric acid, maleic acid, COOH-terminated polycaprolactone, COOH-terminated polyesters or oligoesters such as COOH-terminated poly(ethylene succinate) or poly(hexamethylene adipate). Additional examples of such compounds include, for example, C=C containing groups such as fumaric acid (trans) and maleic acid (cis), among others which react with the diisocyanates via their COOH groups which leave unreacted double bonds available for further derivation by different mechanisms. Indeed, a large number of molecules are able to start the polymerization step including polyaminoacids, saccharides, etc. One example may be a polymer where lactide dimer (LD) is not started by a PEG chain, but rather by butane diol. A pentamer will be formed with HDI and chain-extended using, for example, PEG 6000. Alternatively, one can generate the HDI-PEG6000-HDI macrodiisocyanate and react such a molecule with, for example, (LA)-BD-(LA)4 triblock to produce the material -(HDI)-(LA)-BD-(LA)4-HDI-PEG6000-. A huge number of alternative embodiments are contemplated by the present invention.

When such compounds are used to make AB diblocks, the difunctional diol, diamine or dicarboxylic acid compounds may be terminated with an unreactive or blocking group at one end of the compound, or, alternatively, the compound may simply be end-capped with an unreactive group such as an alkyl, cycloalkyl, aryl, aralkyl or related group including a substituted alkyl, cycloalkyl, aryl or aralkyl group. In such a case where a blocking group is used, the blocking group may be "deblocked" thus producing an AB diblock which has reactive groups at the terminal end of the A block and at the terminal end of the B block. Alternatively and preferably, where the B block is simply end-capped with an unreactive, inert group, the resulting AB diblock will have but one functional group at the terminal end of the A block, which is chain-extended, coupled or crosslinked to multi-diblocks according to the present invention.

The B or C block may vary in size from about 100 Da (dalton units) up to about 200,000 Da or higher, with a preferred range of about 1,000 Da up to about 20,000 Da. Most preferably, the B block is a poly(ethylene oxide) ranging in size from about 3,000 to about 10,000 Da. It is unexpectedly found that the poly(ethyleneoxide) B (or C) block provides the greatest inhibition or reduction in adhesion in the present invention.

The AB diblock or ACA triblock is preferably end-capped with nucleophilic moieties such as hydroxyl or amine groups. Alternatively, these diblocks and triblocks may be end-capped with carboxyl groups as well. With the preferred nucleophilic end-capping groups in place, the AB diblock or ACA triblock may be readily coupled or chain extended using difunctional electrophilic compounds such as diisocyanate or dicarboxylic acid compounds (or derivatives of dicarboxylic acids such as esters or diacyl halides). More preferably, the diblocks and triblocks are end-capped with hydroxyl groups and coupled or chain extended with diisocyanate compounds in order to produce the preferred polymers according to the present invention.

In one aspect, therefore, the present invention relates to a method of substantially reducing or preventing tissue adhesions in patients comprising exposing damaged tissue in a patient to a polymeric composition in a structure such as a film, gel, dispersion, liquid polymer, spray or viscous solution form comprising a multiblock polymer according to the present invention. Structures such as films which incorporate the polymers according to the present invention are preferably characterized by their favorable flexibility, mechanical strength and suture-holding ability as well as being substantially non-water soluble, chain extended, integral and biodegradable. Other structures used in the present invention, as well as gels, viscous solutions and emulsions, in certain aspects, may be preferably water soluble. In all aspects according to the present invention, certain embodiments may be substantially non-water soluble or water soluble, depending upon a variety of factors which may be influenced by treatment and/or delivery of the present compositions to a site of activity.

Preferably, the molecular weight of triblocks, diblocks and polymers used in the present invention are relatively homogeneous which provides for advantageous characteristics in films and related structures, gels, dispersions, sprays, liquid polymers and solutions/emulsions.

In various materials according to the present invention which are included in preformed and non-preformed materials such as films, viscous solutions, suspensions and gels, among others, the polymers may comprise ACA triblocks or AB diblocks as disclosed hereinabove, which may be chain extended, coupled and/or crosslinked using a highly water soluble/water dispersible chain extender or crosslinking agent. Although in many preferred embodiments the B (or C) block of the ACA triblock or AB diblock is hydrophilic and will have a high degree of compatibility with water, thus allowing certain of the polymeric films according to the present invention to absorb large quantities of water or dissolve in water, it is the hydrophilic chain extender or coupler used in various polymers according to the present invention which utilize hydrophobic and hydrophilic B blocks, which allows delivery of these polymer compositions in aqueous solutions. Although in certain aspects of the present invention the ACA triblocks and AB diblocks are preferably non-water soluble (especially, for example, in the case of films and in other aspects of the present invention), in a number of aspects of the present invention including films, or other preformed structures, and in viscous solutions, gels, dispersions and sprays, the use of ACA triblocks and AB diblocks which are substantially water soluble may be advantageous. One of ordinary skill will readily know how to modify the polymers according to the present teachings in an effort to adjust the formulations to maximize delivery within a particular treatment context.

In the present application, the following chain extenders or coupling agents find use in preparing pre-polymerized, non-preformed polymers such as gels and viscous solutions having desirable characteristics for reducing or preventing post-operative adhesion:

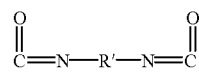

where R' is a $C_2$ to $C_{12}$, preferably a $C_2$ to $C_8$ alkylene group, a cycloalkyl or cycloalkyl-containing group, an aryl or aryl-containing group, 4,4'-diphenylmethane, toluene, naphthalene, 4,4'-dicyclohexylmethane, cyclohexyl, 3,3'-dimethylphenyl, 3,3'-dimethyl-diphenylmethane, 4,6'-xylylene, 3,5, 5-trimethylcyclohexyl, 2,2,4-trimethylhexamethylene or p-phenylene. Equivalents of diisocyanates may also be used as chain extenders in the present invention. Preferred chain extenders may include water soluble macrodiisocyanates including isocyanate terminated poly(oxyalkylene) diisocyanates or isocyanate-terminated polymers comprising poly(ethylene oxide), polyethylene oxide)-co-poly(propylene oxide) and poly(ethylene oxide) containing and poly(ethylene oxide) rich chains, which may be water-soluble or non-water soluble, among others.

Additional preferred chain extenders for use in the present invention include, example those according to the formula:

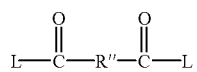

where R" is a $C_0$ to $C_{12}$, preferably a $C_2$ to $C_8$ alkylene group or a hydroxyl or carboxylic acid substituted alkylene group, alkene, a cycloalkyl, hydroxyl or carboxylic acid containing cycloalkyl or cycloalkyl-containing group, an aryl or aryl-containing group or a poly(oxyalkylene) chain comprised of poly(ethylene oxide), poly(ethylene oxide)-co-poly(propylene oxide) or other poly(ethylene oxide) containing or poly(ethylene oxide) rich chains [i.e., where poly(ethylene oxide) is included in an amount ranging from at least about 50% by weight of the polymeric chain and] L is hydroxyl, a halide such as Cl, I or Br or an ester group which can be prepared from a hydroxyl group such as an alkyl, phenyl, benzyl or substituted alkyl, phenyl or benzyl group, include activated ester groups such as a tosyl group, mesyl group or related activated groups. It is noted that diacids according to this aspect of the present invention may also find use as C blocks in certain ACA triblocks and AB diblocks according to the present invention.

It is noted that in choosing ACA triblocks or AB diblocks for formulating viscous solutions and gels according to the present invention, care must be given to providing a good balance of strength/structural integrity and biodegradability from the A block, hydrophilicity/anti-adhesion activity from the C block and further hydrophilicity in the form of water solubility/water dispersibility from the chain extender, coupling agent and/or crosslinking agent, where such agent is used. Notwithstanding certain of the embodiments previously discussed, in the present invention, non-water soluble triblocks or diblocks such as are utilized in film applications according to the present invention also may be advantageously employed in viscous solution/gel applications.

The above-described chemical formulas provide insight into the chain extended and crosslinked polymers which are used in the present invention. In the case of polymers which are preferably used in non-preformed polymers such as gels, dispersions, sprays and/or viscous solutions according to the present invention, the ultimate polymeric composition is preferably water soluble/dispersible and the polymers are preferably chain extended or crosslinked utilizing hydrophilic chain extenders or crosslinking agents, for example, diisocyanate terminated poly(alkylene glycol) chains comprising a central polyalkylene glycol chain such as poly(ethylene oxide), capped by two diisocyanate compounds, among numerous others. Examples include the use of poly(ethylene glycol) chains with a molecular range between 200 and 20,000, hexamethylene diisocyanate or a related diisocyanate as previously described being the diisocyanate. By employing non-water soluble or water soluble ACA triblocks or AB diblocks and preferably employing water soluble/dispersible chain extenders and/or crosslinking agents, polymer compositions which are used in viscous solution and gel applications provide favorable strength and structural integrity, biodegradability (the rate of which may be influenced by the length and hydrophobicity of the A block and the overall hydrophilicity of the polymer), flexibility and anti-adhesion activity from the PEG segments in the polymer and water solubility/dispersibility from the selective chain extenders which are used.

In addition to being useful for substantially reducing, or preventing adhesions, the present polymers may also be used to deliver bioactive compositions to a site of activity within the patient's body. This aspect of the present invention is secondary to the anti-adhesion characteristics of the inventive polymers. It is particularly advantageous that the present polymers may be used to deliver bioactive agents which may serve to enhance the healing of the wounds created by a surgical procedure, a disease state or other condition associated with the tissue to be treated.

Exemplary bioactive agents which may be delivered pursuant to the methods according to the present invention include, for example, anticoagulants, for example heparin and chondroitin sulphate, fibrinolytics such as tPA, plasmin, streptokinase, urokinase and elastase, steroidal and non-steroidal anti-inflammatory agents such as hydrocortisone, dexamethasone, prednisolone, methylprednisolone, promethazine, aspirin, ibuprofen, indomethacin, ketorolac, meclofenamate, tolmetin, calcium channel blockers such as diltiazem, nifedipine, verapamil, antioxidants such as ascorbic acid, carotenes and alpha-tocopherol, allopurinol, trimetazidine, antibiotics, especially noxythiolin and other antibiotics to prevent infection, prokinetic agents to promote bowel motility, agents to prevent collagen crosslinking such as cis-hydroxyproline and D-penicillamine, and agents which prevent mast cell degranulation such as disodium chromoglycate, among numerous others.

In addition to the above agents, which generally exhibit favorable pharmacological activity related to promoting wound healing, reducing infection or otherwise reducing the likelihood that an adhesion will occur, other bioactive agents may be delivered by the polymers of the present invention include, for example, amino acids, peptides, proteins, including enzymes, carbohydrates, antibiotics (treat a specific microbial infection), anti-cancer agents, neurotransmitters, hormones, immunological agents including antibodies, nucleic acids including antisense agents, fertility drugs, psychoactive drugs and local anesthetics, among numerous additional agents.

The delivery of these agents will depend upon the pharmacological activity of the agent, the site of activity within the body and the physicochemical al characteristics of the agent to be delivered, the therapeutic index of the agent, among other factors. One of ordinary skill in the art will be able to readily adjust the physicochemical characteristics of the present polymers and the hydrophobicity/hydrophilicity of the agent to be delivered in order to produce the intended effect. In this aspect of the invention, bioactive agents are administered in concentrations or amounts which are effective to produce an intended result. It is noted that the chemistry of polymeric composition according to the present invention can be modified to accommodate a broad range of hydrophilic and hydrophobic bioactive agents and their delivery to sites in the patient.

Synthesis of Polymers According to the Present Invention

In general, the synthesis of the present polymers proceeds by first synthesizing an AB diblock. In this general reaction, a monofunctional amine, alcohol or carboxyl containing compound is (which preferably includes a compound containing a polyoxyalkylene group) is preferably reacted with a hydroxyacid, its cyclic dimer or a related monomer as previously described herein, to produce the AB diblock. Essentially, the monofunctional amine, alcohol or carboxyl containing compound reacts with the hydroxyacid or its cyclic dimer to produce an AB diblock which is end-capped with a hydroxyl group or other functional group(s) capable of reacting with a coupling agent or crosslinking agent.

Once the AB diblock is formed, the hydroxyl groups at the end(s) of the molecule are reacted with difunctional chain extenders or couplers, for example, diisocyanates. This reaction produces a chain extended polymer (e.g. a diblock or a star or comb polymer) which is readily used to prepare films and various related structures, gels, dispersions, suspensions, pastes and viscous solutions of the present invention. In the case of certain polymers, these are of sufficiently low molecular weight so that they are in liquid form without the need to add additional solvent.

Generally, during the first stage of the reaction in which the low molecular weight AB diblock is formed, the overall molecular weight and the length of the different segments will be determined by the molecular weight of the B block chosen to initiate the reaction, by the number of moles of hydroxyacid, its cyclic dimer or related compounds used to form the A block, which is reacted with the B block. Thereafter, the AB diblock is chain extended, coupled and/or crosslinked to produce polymers containing AB diblocks.

In the case of the use of ACA triblocks, the triblock is first synthesized utilizing a C block which is difunctional diol, diamine or dicarboxylic compound, preferably, a (poly)oxyalkylene diol, most preferably a (poly)ethylene oxide-containing diol which is preferably reacted with a hydroxyacid, its cyclic dimer or a related monomer as previously described herein, to produce the ACA triblock. Once the triblock is formed, it is reacted with a molar excess (most preferably, a 2:1 molar ratio) of chain-extender or coupling agent to produce an intermediate ACA block which is end-capped with coupling agent having on each end a reactive group, which is further reacted with a monofunctional amine, alcohol or carboxyl containing molecule to produce an ACA triblock containing pentameric polymer composition. In this reaction, essentially, the monofunctional amine, alcohol or carboxyl containing compound reacts with chain-extended or coupled ACA triblock to produce the pentamer accordingly.

A particularly preferred synthesis according to the present invention relies on the use of the cyclic ester or lactone of lactic acid and glycolic acid. The use of lactide or glycolide as the reactant will enhance the production of ACA triblocks or AB diblocks which have relatively narrow molecular weight distributions and low polydispersity.

In this preferred method, lactide or glycolide (the cyclic dimer of lactic acid or glycolic acid, respectively), rather than lactic acid or glycolic acid, is first used to synthesize the ACA triblock or AB diblock from the starting poly(oxyalkylene) block. Once the triblock or diblock is obtained, the hydroxyl end-capped triblock or diblock is reacted with a diisocyanate, preferably hexamethylene diisocyanate.

The synthesis of the ACA triblock or Ab diblock preferably proceeds by way of a ring-opening mechanism, whereby the ring opening of the lactide or glycolide is initiated by the hydroxyl end groups of the diol, diamine or dicarboxyl (preferably, PEG) chain under the influence of a catalyst such as stannous octoate. An ACA type triblock or AB type diblock is generated at this point, the molecular weight of which is a function of both the molecular weight of the central B or C block, preferably a PEG chain, and the length of the polyester, preferably PLA, lateral block(s). Typically, the molecular weight of the triblock ranges from about 4,000 to about 30,000 (but may be as low as 1,000 or less and as high as 250,000 or more). In the case if the diblock, the molecular weight may range as low as several hundred to upwards of 50,000 or more. After synthesis of the ACA triblock or AB diblock, the final polymer is preferably obtained by chain extending the hydroxyl terminated triblocks with difunctional reactants such as isocyanates, most preferably hexamethylene diisocyanate.

The chemical and physical properties of the different polymers will vary as a function of different parameters, the molecular weight and composition of the B (or C) block and A block segments along the backbone of the AB diblocks and ACA triblocks being of particular importance.

The preferred method has several advantageous characteristics including:
1. a rapid, nearly quantitative reaction which is complete in from 1 to 3 hours;
2. the reaction takes place under moderate reaction conditions (140° C.) thus minimizing side reactions;
3. the resulting triblock or diblock contains an extremely narrow polydispersity (P=1.3-1.4 or better; and
4. the triblock or diblock contains little or no homopolymer.

Preparation of Adhesion Barrier Structures

Barrier structures (which term includes films as well as cylinders and related three-dimensional structures) for use in the present invention are prepared by first producing the polymer according to the present invention and then dissolving the polymer in a solvent, such as chloroform, methylene chloride or a related organic solvent. Films, for example, are preferably prepared by placing the solution containing polymer in a mold or a related receptacle and then allowing the solvent to evaporate. The resulting film is homogeneous and of uniform thickness and density. The film may be used as prepared or cut into segments for application to a desired site in a patient. In addition to the above-described solvent cast method, a continuous solvent cast process, a thermal cast method or related methods well known in the art may be used to make films and other structures according to the present invention.

In order to prepare other three dimensional structures of polymer, such as cylinders and related shapes, these may be cast or molded using various techniques, starting with solid polymer. Methods to produce these structures using these techniques are well known in the art.

Preparation of Gels, Viscous Solutions and Dispersions

In order to prepare the gels, viscous solutions, pastes and dispersions according to the present invention, polymer in powder, flakes or other related form is dissolved or suspended in an aqueous solution, preferably sterile isotonic saline solution, generally at room temperature and then mixed in the solution to produce the final gel, viscous solution or dispersion. Viscosity of the system is readily adjusted by adding further polymer or aqueous solution. The gels, viscous solutions, pastes and dispersions are utilized under sterile conditions when they are applied in medical applications.

While not being limited by way of theory, it is believed that the chain extended polymers of the present invention form integral layers in films, gels or viscous solutions when applied to tissue for surgical applications. The resulting integral polymers provide an excellent barrier which substantially reduces the formation of post-operative adhesions.

Having generally described the invention, reference is now made to the following examples intended to illustrate preferred embodiments and comparisons but which are not to be construed as limiting to the scope of this invention as more broadly set forth above and in the appended claims.

EXAMPLES

The synthesis of the polymers is presented in the following examples. In general, where solvent is used, it is dried and distilled prior to use. Nitrogen is used dry at all times. All other materials are dried and distilled prior to use.

Example 1

Synthesis of [MPEG 750-d,lLA4]2-HDI

The synthesis consisted of two consecutive stages, namely the diblock synthesis and the consequent di-diblock formation.

1. Diblock Synthesis 80 gr. of poly(ethylene glycol) methyl ether of molecular weight 750 (MPEG 750), was dried under vacuum at 100+ C. for 1 hour, under constant stirring. 32.26 gr. of (d,l)lactide were then added, corresponding to an LA:PEG molar ratio 4:1, including an excess of 5%. Catalyst (stannous 2-ethyl hexanoate) was added at a molar ratio of 1/400 of the amount of added lactide, i.e. 0.3 gr. The reaction was carried out in a sealed flask, under a dry nitrogen-saturated atmosphere, for two hours at 145° C.

2. Di-Block Formation

The diblock obtained in the first step was reacted with 17.92 gr. of hexamethylene diisocyanate (HDI) (at a molar ratio of 1:2) in a three-necked flask for 1 hour under mechanical stirring and dry nitrogen atmosphere, at 85° C.

The material is a water-soluable viscous liquid, at room temperature.

Example 2

Synthesis of [MPEG 750-d,lLA8]2-HDI

Same as in EXAMPLE 1, except for the use of 64.51 gr. of (d,l)lactide, corresponding to an LA:PEG molar ratio of 8:1, and 0.43 gr. of catalyst, in the first stage of the synthesis.

The material is a water-soluable viscous liquid, at room temperature.

Example 3

Synthesis of [MPEG 750-d,lLA12]2-HDI

Same as EXAMPLE 1, except for the use of 96.77 gr. of (d,l)lactide corresponding to an LA:PEG molar ratio of 8:1 and 0.68 gr. of catalyst, in the first stage of the synthesis.

The material is a water-insoluble viscous liquid, which does not flow at room temperature.

Example 4

Synthesis of [MPEG 550-(l)LA4-HDI]2-PEG 400

The synthesis consisted of three stages as follows:

1. Diblock Synthesis 70 gr. of poly (ethylene glycol) methyl ether of molecular weight 500 (MPEG 550), was dried under vacuum at 100° C. for 1 hour, under constant stirring. 42.15 gr. of (l)lactide were then added, corresponding to an LA:PEG molar ratio of 4:1, including an excess of 15%. Catalyst (stannous 2-ethyl hexanoate) was added at a molar ration of 1/400 of the amount of added lactide, i.e. 0.296 gr. The reaction was carried out in a sealed flask, under dry nitrogen-saturated atmosphere, for 150 min. at 150° C.

2. Macrodiisocyanate Formation 23.87 gr. of dried poly(ethylene glycol) of molecular weight 400 (PEG 400) were reacted with 20.07 gr. of HDI (corresponding to a 1:2 molar ratio, including a 10% excess of HDI, by adding the PEG 400 to the HDI in a three-necked flask, under mechanical stirring (80 rpm) at room temperature and the reaction was carried out for 10 min. under a dry nitrogen atmosphere, at 75° C.

3. Addition of Diblock 100 gr. of dried diblock were added to the macrodiisocyanate, corresponding to a 2:1 molar ratio. Catalyst (stannous 2-ethyl hexanoate) was added simultaneously at a molar ratio of 1/100 of the amount of the added diblock, i.e. 0.48 gr. The reaction took place under the same conditions as described in step 2.

Thermal analysis of the material showed a glass transition temperature around −41° C. The viscosity of this material was 22000 cps and 5000 cps at 22° C. and 3° C. respectively. The product exhibited a translucid, yellowish color. NMR analysis showed the average number of LA units as 4.06.

Example 5

Synthesis of [MPEG 550-(l)LA2-HDI]2-PEG 400

The synthesis consisted of three stages as follows:

1. Diblock Synthesis 55 gr. of monomethyl ether-terminated poly(ethylene glycol) of molecular weight 550 (MPEG 550), was dried under vacuum at 100° C. for 1 hour, under constant stirring. 14.4 gr. of (l)lactide were then added, corresponding to a molar ratio LA:PEG of 2:1, including an excess of 15%. Catalyst (stannous 2-ethyl hexanoate) was added at a molar ratio of 1/400 of the amount of added lactide, i.e. 0.1 gr. The reaction was carried out in a sealed flask, under dry, nitrogen-saturated atmosphere, for 150 min. at 140° C.

2. Macrodiisocyanate Formation 20 gr. of dried PEG 400 were reacted with 16.82 gr. of HDI (corresponding to a 1:2 molar ratio, by adding the PEG 400 at the HDI in a three-necked flask, under mechanical stirring and nitrogen atmosphere, at 70° C. The reaction was carried out for 4 min.

3. Addition of Diblock 69.4 gr. of diblock were added to the macrodiisocyanate, corresponding to a 2:1 molar ratio. The reaction took place under the same condition as described in step 2, for one hour.

The product was a yellowish liquid at room temperature.

Example 6

Synthesis of [MPEG 550-(l)LA6-HDI]2-PEG 600

The synthesis consisted of three steps as follows:

1. Diblock Synthesis 140 gr. of poly(ethylene glycol) methyl ether weight 550 (MPEG 550), was dried under vacuum at 100° C. for 1 hour, under constant stirring. 126 gr. of L lactide were then added, corresponding to an LA:PEG molar ratio of 6:1, including an excess of 15%. Catalyst (stannous 2-ethyl hexanoate) was added at a molar ratio of 1/400 of the amount of added lactide, i.e. 0.89 gr. The reaction was carried out in a sealed flask, under a dry, nitrogen-saturated atmosphere, for 150 min. at 150° C.

2. Macrodiisocyanate Formation 61 gr. of dried PEG 400 were reacted with 37.62 gr. of HDI (corresponding to a 1:2 molar ratio, including a 10% excess of HDI, by adding the PEG 600 to the HDI in a three-necked flask, under mechanical stirring at 80 rpm and dry nitrogen atmosphere, at 85° C. The reaction was carried out for 10 min.

3. Addition of Diblock 200 gr. of dried diblock were added to the macrodiisocyanate, corresponding to a 2:1 molar ratio. Catalyst (stannous 2-ethyl hexanoate) was added simultaneously at a molar ratio of 1/100 of the amount of added diblock, i.e. 0.82 gr. The reaction took place under the same conditions as described in step 2.

Example 7

Synthesis of [MPEG 550-HDI]2-[(l)LA4-PPG1000-LA4]

The synthesis consisted of three stages as follows:

1. Triblock Synthesis 40 gr. of poly(propylene glycol) of molecular weight 1000 (PPG 1000), were dried under vacuum at 100° C. for 1 hour, under constant stirring. 25.8 gr. of (l)lactide were then added, corresponding to an LA:PEG molar ratio of 8:1, including an excess of 12%. Catalyst (stannous 2-ethyl hexanoate) was added at a molar ratio of 1/400 of the amount of added lactide, i.e. 0.181 gr. The reaction was carried out in a sealed flask, under a dry, nitrogen-saturated atmosphere, for 150 min. at 150° C.

2. Macroisocyanate Formation 34.87 gr. of dried MPEG 550 were reacted with 11.2 gr. of HDI (corresponding to a 1:1 molar ratio, by adding the MPEG 550 to the HDI in a three-necked flask, under mechanical stirring and dry nitrogen atmosphere, at 75° C. Catalyst (stannous 2-ethyl hexanoate) was added at a molar ratio of 1/100 of the amount of added diblock, i.e. 0.82 gr. The reaction was carried out for an hour.

3. Addition of Triblock 50 gr. of dried diblock were added to the macroisocyanate corresponding to a 1:2 molar ratio. The reaction took place under the same conditions as described in step 2.

Thermal analysis of the triblock showed a glass transition temperature around −44° C. and two melting endotherms at 11° C. and 34° C. The viscosity was 43000 cps at 27° C. The product exhibited a translucid white color.

Example 8

Synthesis of (MPEG 550-(d,l)LA30-HDI)2-PCL 1250

The synthesis consisted of three stages as follows:

1. Diblock Synthesis 4.4 gr. of poly(ethylene glycol) methyl ether of molecular weight 550 (MPEG 550), was dried under vacuum at 100° C. for 1 hour, under constant stirring. 19.8 gr. of (d,l)lactide were then added, corresponding to a molar ratio LA:PEG of 30:1, including an excess of 15%. Catalyst (stannous 2-ethyl hexanoate) was added at a molar ratio of 1/400 of the amount of added lactide, i.e. 0.12 gr.

The reaction was carried out in a sealed flask, under a dry, nitrogen-saturated atmosphere, for 150 min. at 140° C.

2. Macrodiisocyanate Formation 5 gr. of dried polycaprolactone of molecular weight 1250 (PCL 1250) were reacted with 1.34 gr. of HDI (corresponding to a 1:2 molar ratio, by adding the PCL 1250 to the HDI in a three-necked flask, under mechanical stirring and dry nitrogen atmosphere, at 70° C. The reaction was carried out for 30 min.

3. Addition of Diblock 24.2 gr of dried diblock were added to the macrodiisocyanate, corresponding to a 2:1 molar ratio. The reaction took place under the same condition as described in step 2, for one hour.

The NMR spectrum showed a 1:4 ratio and the product exhibited a viscosity of 40000 cps at 80° C. At room temperature it appeared as a hard sticky solid.

Example 9

Synthesis of [MPEG 750-(HDI-(l)LA4-PEG400-(l)LA4-HD)]12-[PEG1000]

The synthesis consisted of four stages as follows:

1. Triblock LA4-PEG400-LA4Synthesis

Same as described as in EXAMPLE 4

2. Macrodiisocyanate Formation 17 gr. of triblock were reacted with 6.26 gr. of HDI (corresponding to a 1:2 molar ratio, including a 7% excess of HDI, by adding the triblock to the HDI in a three-necked flask, under mechanical stirring and a dry nitrogen atmosphere, at 85° C.). The reaction was carried of for one hour.

3. Reaction Between Macrodiisocyanate and PEG 1000

8.71 gr. of dried PEG 1000 were added to the reaction, corresponding to a 1:2 molar ratio, and reacted under the same conditions as described in step 2.

4. Addition of MPEG750

13.05 gr. of dried PEG750M were added to the reaction, corresponding to a 2:1 molar ratio, and reacted under the same conditions as described in step 2.

Example 10

Synthesis of [(HexOH-LA12-HD)]2-PCL4000

Same as EXAMPLE 4, except for the use of 4.73 gr. of hexanol and 40 gr. of (d,l)lactide, corresponding to a hexanol:

lactide molar ratio of 1:12 and 0.28 gr. of catalyst in the first stage, the use of 20 gr. of PCL 4000 and 1.68 gr. of HDI in the second stage, to which 44.73 gr. of triblock were added in the third stage.

Example 11

Synthesis of [MPEG 550-d,lLA12-HDI]2-PCL2000

Same as EXAMPLE, except for the use of 20 gr. of MPEG 500 and 36.13 gr. of (d,l)lactide, corresponding to a hexanol: lactide molar ratio of 1:12 and 0.21 gr. of catalyst in the first stage, the use of 20 gr. of PCL 2000 and 3.36 gr. of HDI in the second stage, to which 56.13 gr. of triblock were added in the third stage.

Example 12

Synthesis of [MPEG 750-HDI-PEG6000-HDI]2-[(l)LA4-PEG400-(l)LA44]

The synthesis consisted of four stages as follows:

1. Triblock LA4-PEG400-LA4Synthesis 35 gr. of PEG 400 were dried as in EXAMPLE 1, to which 55.9 gr. of (l) lactide were added, including an excess of 5% 0.0355 gr. of catalyst (stannous 2-ethyl hexanoate) were added at a molar ratio of 1/400 of the amount of added lactide. Reaction was carried out under the same conditions as described in EXAMPLE 1.

2. Macrodiisocyanate Formation 30.72 gr. of dried PEG 6000 were reacted with 2.94 gr. of HDI (corresponding to a 1:2 molar ratio, including a 7% excess of HDI), by adding the PEG 6000 to the HDI in a three-necked flask, under mechanical stirring and nitrogen atmosphere, at 85° C. The reaction was carried out for an hour.

3. Reaction Between Macrodiiscoanate and Triblock 2.5 gr. of triblock were added to the macrodiiscoanate corresponding to a 1:2 molar ratio and reacted under the same conditions as described in step 2.

4. Addition of MPEG750

3.84 gr. of dried MPEG750 were added to the reaction, corresponding to a 2:1 molar ratio, and reacted under same conditions described in step 2.

The material is a white, crystalline, water-soluble solid at room temperature, displaying a melting endotherm at 56° C.

Example 13

Synthesis of [MPEG 750-HDI-PEG2000-HDI]2-[(l)LA4-PEG400-(l)LA4]

The synthesis consisted of four stages as EXAMPLE 4, except for the use of 41 gr. of dried PEG 2000 and 7.38 gr. of HDI in the second stage, 10 gr. of triblock LA4-PEG400-LA4 in the third stage and 15.38 gr. of dried PEG 750M in the fourth stage. Molar ratios between reagents were the same as in EXAMPLE 4, absolute amounts, however, were normalzed to enable the use of 10 gr. of triblock, for convenience purposes The material is a white, crystalline, water-soluable solid at room temperature displaying a melting endotherm at 50° C.

Example 14

Synthesis of [MPEG 750-HDI-PEG1000-HDI]2-[(l)LA4-PEG400-(l)LA4]

The synthesis consisted of four stages as in EXAMPLE 1, except for the use of 40 gr. of dried PEG 1000 and 14.38 gr. of HDI in the second stage, 19.52 gr. of triblock LA4-PEG400-LA4 in the third stage and 30 gr. of dried PEG 750M in the fourth stage.

The material is a yellowish, crystalline, water-soluable solid at room temperature, displaying a melting endotherm at 43° C.

Example 15

Synthesis of [MPEG 750-HDI-PEG600-HDI]2-[(l)LA4-PEG400-(l)LA4]

The synthesis consisted of four stages as in EXAMPLE 4, except for the use of 35 gr. of dried PEG 600 and 20.96 gr. of HDI in the second stage, 28.45 gr. of triblock LA4-PEG400-LA4 in the third stage and 43.73 gr. of dried PEG 750M in the fourth stage.

The material is a yellowish, water-soluable solid at room temperature, displaying a melting endotherm at 22° C.

Example 16

Synthesis of [MPEG 750-HDI-PEG400-HDI]2-[(l)LA4-PEG400-(l)LA]

The synthesis consisted of four stages as in EXAMPLE 4, except for the use of 24 gr. of dried PEG 400 and 22.47 gr. of HDI in the second stage, 30.5 gr. of triblock LA4-PEG4LA4 in the third stage and 46.88 gr. of dried PEG 750M in the fourth stage.

The material is a yellowish, water-soluable solid at room temperature, displaying a melting endotherm at 19° C.

Example 17

Synthesis of [MPEG 750-HDI-PEG400-HDI]2-[(d,l)LA4-PEG400-(d,l)LA4]

The synthesis consisted of four stages as in EXAMPLE 4, except for the use of (d,l)lactide for the triblock preparation, instead of (l)lactide.

Example 18

Synthesis of {PEG600-(HDI-(d,l)LA4-PPG1000-(d,l)LA4-HDI)-PEG60012-[HDI]

The synthesis consisted of four stages as follows:

1. Triblock Synthesis 40 gr. of poly (propylene glycol) of molecular weight 1000 (PPG 1000), were dried under vacuum at 100° C. for 1 hour, under constant stirring. 25.8 gr. of (d,l)lactide were then added, corresponding to a molar ration LA:PEG of 8:1, including excess of 12%. Catalyst (stannous 2-ethyl hexanoate) was added at a molar ratio of 1/400 of the amount of added lactide, i.e. 0.181 gr. The reaction was carried out in a sealed flask, under a dry, nitrogen-saturated atmosphere, for 150 min at 150° C.

2. Macrodiisocyanate Formation 20 gr. of dried triblock were reacted with 4.57 gr. of HDI (corresponding to a 1:2 molar ratio), by adding the triblock to the HDI (+1 ml of chloroform, used to quantitatively add the HDI and catalyst) in a three-necked flask, under mechanical stirring and dry nitrogen atmosphere, at 75° C. Catalyst (stannous 2-ethyl hexanoate) was added at a molar ratio of 1/50 of the amount of added lactide, i.e. 0.103 gr. The reaction was carried out for 15 min.

3. Addition of PEG 600

15.23 gr. of dried PEG 600 were added to the macrodiisocyanate, corresponding to a 2:1 molar ratio. The reaction took place under the same conditions as described in step 2.

4. Addition of HDI 1.14 gr. of HDI, corresponding to a 2:1 molar ratio in relation with the triblock, including an excess of 7% were added (+1 ml of chloroform, used to quantitatively add the HDI and catalyst) and reacted for an hour as described before.

The material exhibited a translucid white color. The triblock showed a glass transition temperature of −39° C., the average number of LA units being 5.2, as determined by NMR.

It is to be understood that the examples and embodiments described hereinabove are for the purposes of providing a description of the present invention by way of example and are not to be viewed as limiting the present invention in any way. Various modifications or changes that may be made to that described hereinabove by those of ordinary skill in the art are also contemplated by the present invention and are to be included within the spirit and purview of this application and the following claims.

The invention claimed is:

1. A biodegradable or bioerodible polymeric composition consisting essentially of hydrophilically crosslinked AB diblocks, where A is a polyester unit derived from the polymerization of monomers selected from the group consisting of lactic acid, lactide, glycolic acid, glycolide, β-propiolactone, ε-caprolactone, δ-glutarolactone, δ-valerolactone, β-butyrolactone, pivalolactone, α,α-diethylpropiolactone, ethylene carbonate, trimethylene carbonate, γ-butyrolactone, p-dioxanone, 1,4-dioxepan-2-one, 3-methyl-1,4-dioxane-2,5-dione, 3,3,-dimethyl-1-4-dioxane-2,5-dione, cyclic esters of α-hydroxybutyric acid, α-hydroxyvaleric acid, α-hydroxyisovaleric acid, α-hydroxycaproic acid, α-hydroxy-α-ethylbutyric acid, α-hydroxyisocaproic acid, α-hydroxy-α-methyl valeric acid, α-hydroxyheptanoic acid, α-hydroxystearic acid, α-hydroxylignoceric acid, salicylic acid and mixtures, thereof and B is a polyoxyalkylene polymer which is end-capped with a non-reactive group, said AB diblock being further reacted with one or more water soluble or water dispersible crosslinking agents to produce crosslinked diblock polymers wherein said crosslinking agents comprise (poly)ethylene oxide chains or (poly)ethylene oxide-co-(poly)propylene oxide chains.

2. The composition according to claim 1 wherein said non-reactive group is an alkyl, aryl, aralkyl, substituted alkyl, substituted aryl, substituted aralkyl, a protecting group or a —C═C— containing group.

3. The composition according to claim 2 wherein said non-reactive group is a $C_1$-$C_{12}$ alkyl group.

4. The composition according to claim 1 wherein said polyester comprises poly(hydroxy carboxylic acid).

5. The composition according to claim 1 wherein said polyester is obtained from polymerization of an aliphatic hydroxycarboxylic acid or ester selected from the group consisting of L-lactic acid, D,L-lactic acid, glycolic acid, L-lactide, D,L-lactide, glycolide, caprolactone or mixtures thereof.

6. The composition according to claim 2 wherein said non-reactive group is an optionally substituted alkyl group.

7. The composition according to claim 6 wherein said non-reactive group is a methyl group.

8. The composition according to claim 7 wherein said polyoxyalkylene polymer is a polyethyleneoxide polymer.

9. The composition according to claim 1 wherein A is a polyester unit derived from the polymerization of lactide monomers.

10. The composition according to claim 2 wherein A is a polyester unit derived from the polymerization of lactide monomers.

11. The composition according to claim 3 wherein A is a polyester unit derived from the polymerization of lactide monomers.

12. The composition according to claim 6 wherein A is a polyester with derived from the polymerization of lactide monomers.

13. The composition according to claim 7 wherein A is a polyester unit derived from the polymerization of lactide monomers.

14. The composition according to claim 8 wherein A is a polyester unit derived from the polymerization of lactide monomers.

15. The composition according to claim 9 wherein said polyoxyalkylene polymer is a polyethyleneoxide polymer.

16. The composition according to claim 10 wherein said polyoxyalkylene polymer is a polyethyleneoxide polymer.

17. The composition according to claim 11 wherein said polyoxyalkylene polymer is a polyethyleneoxide polymer.

18. The composition according to claim 12 wherein said polyoxyalkylene polymer is a polyethyleneoxide polymer.

19. The composition according to claim 13 wherein said polyoxyalkylene polymer is a polyethyleneoxide polymer.

* * * * *